(12) United States Patent
Akatsu et al.

(10) Patent No.: US 10,390,735 B2
(45) Date of Patent: Aug. 27, 2019

(54) BODY STATE DETECTING APPARATUS, BODY STATE DETECTING METHOD AND BED SYSTEM

(71) Applicants: MINEBEA MITSUMI Inc., Nagano (JP); NATIONAL UNIVERSITY CORPORATION CHIBA UNIVERSITY, Chiba (JP)

(72) Inventors: Hiroyuki Akatsu, Tokyo (JP); Kunihiko Sato, Fujisawa (JP); Norihito Iida, Sagamihara (JP); Shiroh Isono, Chiba (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 15/880,947

(22) Filed: Jan. 26, 2018

(65) Prior Publication Data

US 2018/0146889 A1 May 31, 2018

Related U.S. Application Data

(63) Continuation of application No. PCT/JP2016/072325, filed on Jul. 29, 2016.

(30) Foreign Application Priority Data

Jul. 30, 2015 (JP) ................... 2015-151220
Oct. 27, 2015 (JP) ................... 2015-210438
Jul. 13, 2016 (JP) ................... 2016-138506

(51) Int. Cl.
*A61B 5/103* (2006.01)
*A61B 5/113* (2006.01)
(Continued)

(52) U.S. Cl.
CPC .............. *A61B 5/1036* (2013.01); *A61B 5/11* (2013.01); *A61B 5/113* (2013.01); *A61B 5/1116* (2013.01);
(Continued)

(58) Field of Classification Search
CPC ....... A61B 5/1036; A61B 5/11; A61B 5/1116; A61B 5/113; A61B 5/4818; A61B 5/6891; A61B 5/7278; A61G 7/0527; A61G 7/05
(Continued)

(56) References Cited

U.S. PATENT DOCUMENTS 6,280,392 B1  8/2001  Yoshimi et al.
9,757,295 B2  9/2017  Miyashita et al.
(Continued)

FOREIGN PATENT DOCUMENTS

CN    101313877 A   12/2008
CN    202859498 U   4/2013
(Continued)

OTHER PUBLICATIONS

English Translation of JP 2009240660 (Year: 2009).*
(Continued)

*Primary Examiner* — Daniel L Cerioni
(74) *Attorney, Agent, or Firm* — Pearne & Gordon LLP

(57) ABSTRACT

There is provided a body state detecting apparatus for detecting a body state of a subject on a bed, the apparatus including: a plurality of load detectors which are placed in the bed or under feet of the bed and which detect a load variation depending on a respiration of the subject; and a body state detecting unit which determines an extending direction of a body axis of the subject and a head placement of the subject based on the detected load variation. The body state detecting unit includes a body axis direction determin-
(Continued)

ing unit which determines the extending direction of the body axis of the subject based on the detected load variation, and a head placement determining unit which determines the head placement of the subject, in the determined extending direction of the body axis of the subject, based on the detected load variation.

22 Claims, 20 Drawing Sheets

(51) Int. Cl.
    *A61B 5/00*         (2006.01)
    *A61G 7/05*         (2006.01)
    *A61B 5/11*         (2006.01)

(52) U.S. Cl.
    CPC .......... *A61B 5/4818* (2013.01); *A61B 5/6891* (2013.01); *A61B 5/7278* (2013.01); *A61G 7/05* (2013.01); *A61G 7/0527* (2016.11); *A61G 2203/20* (2013.01); *A61G 2203/32* (2013.01); *A61G 2203/70* (2013.01)

(58) Field of Classification Search
    USPC ........................................................ 600/587
    See application file for complete search history.

(56) References Cited

U.S. PATENT DOCUMENTS

| | | | |
|---|---|---|---|
| 9,907,716 | B2 | 3/2018 | Miyashita et al. |
| 2005/0107722 | A1 | 5/2005 | Ozaki et al. |
| 2008/0312516 | A1 | 12/2008 | Ozaki et al. |
| 2015/0164721 | A1 | 6/2015 | Miyashita et al. |
| 2017/0281439 | A1 | 10/2017 | Miyashita et al. |

FOREIGN PATENT DOCUMENTS

| | | | |
|---|---|---|---|
| CN | 104582661 | A | 4/2015 |
| JP | S53-92577 | A | 8/1978 |
| JP | 07-327939 | H | 12/1995 |
| JP | 2003-000552 | A | 1/2003 |
| JP | 2005-144042 | A | 6/2005 |
| JP | 4002905 | B2 | 11/2007 |
| JP | 2008-264338 | A | 11/2008 |
| JP | 2009-240660 | A | 10/2009 |
| JP | 2011-120667 | A | 6/2011 |
| JP | 4829020 | B2 | 11/2011 |
| JP | 2012-011174 | A | 1/2012 |
| JP | 2014-180432 | A | 9/2014 |

OTHER PUBLICATIONS

English Translation of JP 2003000552 (Year: 2003).*
International Search Report for corresponding International Application No. PCT/JP2016/072325 dated Oct. 25, 2016.
Notice of Reasons for Rejection for corresponding Japanese Patent Application No. 2016-138506 dated Oct. 18, 2016 and partial English translation.
Notice of Reasons for Rejection for corresponding Japanese Patent Application No. 2016-138506 dated Jan. 31, 2017 and partial English translation.
Decision to Grant a Patent, dated Feb. 17, 2017, and partial English translation.
English Translation of Written Opinion for corresponding International Application No. PCT/JP2016/072325 dated Oct. 25, 2016.
International Preliminary Report on Patentability for corresponding International Application No. PCT/JP2016/072325 dated Jan. 30, 2018.
Extended European Search Report dated Mar. 7, 2019 for corresponding European Application No. 16830609.0.
Chinese Office Action dated Mar. 14, 2019 for corresponding ChineseApplication No. 201680044026.3 and English translation.

* cited by examiner

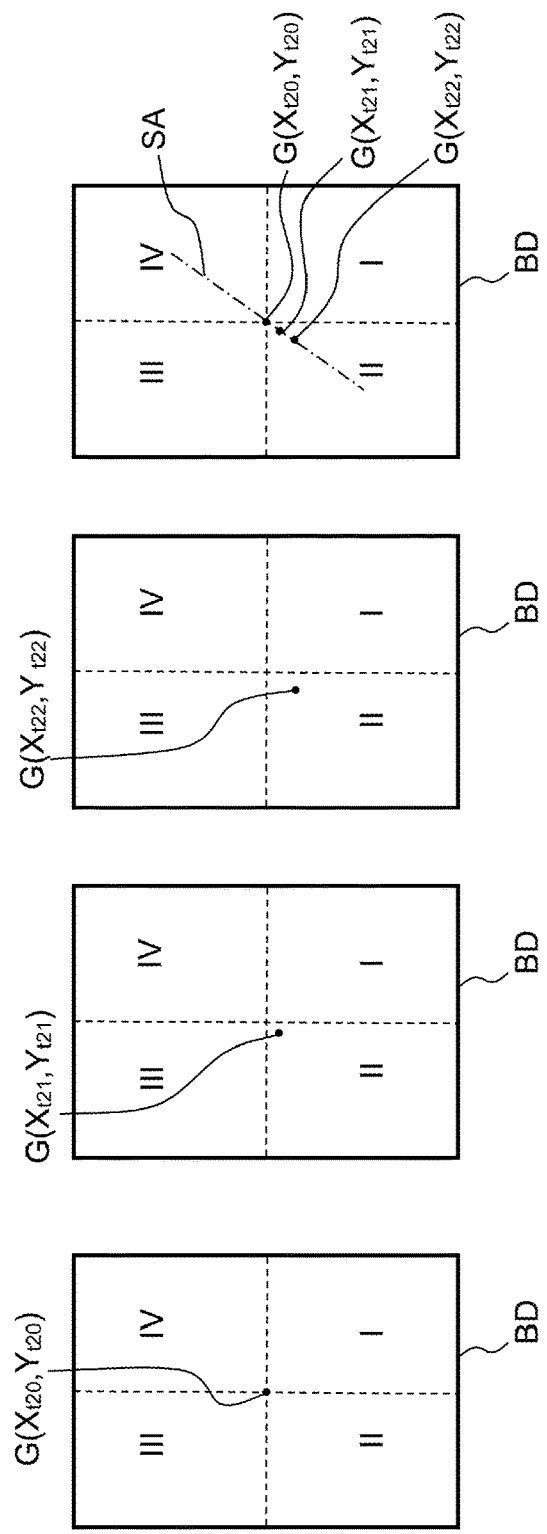

BODY STATE DETECTING APPARATUS, BODY STATE DETECTING METHOD AND BED SYSTEM

CROSS-REFERENCE TO RELATED APPLICATIONS

This application is a Continuation Application of International Application No. PCT/JP2016/072325 claiming the conventional priority of Japanese patent Application No. 2015-151220 filed on Jul. 30, 2015, Japanese patent Application No. 2015-210438 filed on Oct. 27, 2015 and Japanese patent Application No. 2016-138506 filed on Jul. 13, 2016, and titled "PHYSICAL CONDITION DETECTING DEVICE, PHYSICAL CONDITION DETECTING METHOD AND BED SYSTEM". The disclosures of Japanese patent Applications No. 2015-151220, No. 2015-210438, and No. 2016-138506 and International Application No. PCT/JP2016/072325 are incorporated herein by reference in their entirety.

BACKGROUND

The present disclosure relates to body state detecting apparatus (physical condition detecting device) using a load detector(s), and a bed system including the body state detecting apparatus. Further, the present disclosure relates to a body state detecting method (physical condition detecting method) using the load detector(s).

Systems for managing, from a remote place, patients and/or persons receiving nursing care on their beds are utilized in hospitals, care facilities and the like. For example, if a system is used in a hospital to detect a patient's present (exist, settling) on/leaving (absent) from the bed, then the nurses in the nurse station can check whether or not the patient is on the bed in his/her room without visiting the room.

Japanese Patent Application Laid-open No. 2008-264338 discloses a present-on-the-bed detecting method in which a load detecting means are arranged under each of the four feet of a bed so as to determine whether or not a subject is present on the bed on the basis of the outputs of those load detecting means. Further, Japanese Patent Application Laid-open No. 2014-180432 discloses a motion detecting apparatus configured to identify the center of gravity position of a subject on the bed on the basis of the outputs of four load sensors arranged respectively under the four feet of the bed.

SUMMARY

However, with the present-on-the-bed detecting method disclosed in Japanese Patent Application Laid-open No. 2008-264338 and/or the motion detecting apparatus disclosed in Japanese Patent Application Laid-open No. 2014-180432, although it is possible to know whether a subject is present on or absent from the bed, and/or his/her center of gravity position, it is difficult to determine the subject's body state (body condition, body situation, physical condition) such as the orientation of the body and/or the head, the posture, and the like. If such information about the body state is available, especially information about the body state of the subject in sleep, without using a video-recording device, then it is extremely useful for improving (alleviating) such symptoms as the sleep apnea syndrome (SAS), snore, and the like.

In view of the above, an object of the present disclosure is to provide a body state detecting apparatus, a body state detecting method, and a bed system which are capable of detecting the body state of a subject on the bed in a detailed manner on the basis of the detection of a load sensor(s).

According to a first aspect of the present disclosure, there is provided a body state detecting apparatus for detecting a body state of a subject on a bed, the apparatus including:

a plurality of load detectors which are placed in the bed or under feet of the bed and which detect a load variation depending on a respiration of the subject; and a body state detecting unit which determines an extending direction of a body axis of the subject and a head placement of the subject based on the detected load variation, wherein the body state detecting unit includes a body axis direction determining unit which determines the extending direction of the body axis of the subject based on the detected load variation, and a head placement determining unit which determines the head placement of the subject, in the determined extending direction of the body axis of the subject, based on the detected load variation.

According to a second aspect of the present disclosure, there is provided a body state detecting apparatus for detecting a body state of a subject on a bed, the apparatus including:

a plurality of load detectors which are placed in the bed or under feet of the bed and which detect a load variation depending on a respiration of the subject; and a body state detecting unit which determines an extending direction of a body axis of the subject and a head placement of the subject based on the detected load variation, wherein the body state detecting unit determines the head placement of the subject based on a waveform exhibiting the detected load variation.

According to a third aspect of the present disclosure, there is provided a bed system including:

a bed; and the body state detecting apparatus according to the first aspect.

According to a fourth aspect of the present disclosure, there is provided a body state detecting method for detecting a body state of a subject on a bed, the method including:

detecting a load variation depending on a respiration of the subject with a plurality of load detectors placed in the bed or under feet of the bed; and determining an extending direction of a body axis of the subject and a head placement of the subject based on the detected load variation, wherein the extending direction of the body axis of the subject is determined based on the detected load variation, and then the head placement of the subject is determined, in the determined extending direction of the body axis of the subject, based on the detected load variation.

According to a fifth aspect of the present disclosure, there is provided a body state detecting method for detecting a body state of a subject on a bed, the method comprising:

detecting a load variation depending on a respiration of the subject with a plurality of load detectors placed in the bed or under feet of the bed; and determining an extending direction of a body axis of the subject and a head placement of the subject based on the detected load variation, wherein the head placement of the subject is determined based on a waveform exhibiting the detected load variation.

According to a sixth aspect of the present disclosure, there is provided a body state detecting apparatus for detecting a body state of a subject on a bed, the apparatus including:

a plurality of load detectors which are placed in the bed or under feet of the bed and which detect a load variation depending on a respiration of the subject; and a body state detecting unit which determines a head placement of the subject based on the detected load variation.

BRIEF DESCRIPTION OF THE DRAWINGS

FIGS. 7A to 7D are illustrative views depicting an image of the movement of the center of gravity position of the subject on the bed, and an extending direction of the body axis of the subject, wherein FIGS. 7A, 7B, and 7C depict the center of gravity positions of the subject at the times $t_{20}$, $t_{21}$, and $t_{22}$, respectively; and FIG. 7D depicts the extending direction of the body axis of the subject, overlaid with the center of gravity positions of the subject at the respective times.

FIGS. 8A and 8B depict schematic images of a variation in detected values of the load detectors caused by the respiration of the subject, wherein FIG. 8A depicts the image of the variation in detected values fed from the load detectors arranged at the head side of the subject while FIG. 8B depicts the image of the variation in detected values fed from the load detectors arranged at the feet side of the subject.

FIGS. 9A and 9B depict other exemplary schematic images of the variation in detected values of the load detectors caused by the respiration of the subject, wherein FIG. 9A depicts the other exemplary image of the variation in detected values fed from the load detectors arranged at the head side of the subject while FIG. 9B depicts the other exemplary image of the variation in detected values fed from the load detectors arranged at the feet side of the subject.

FIGS. 11A, 11B, and 11C depict schematic images of the variation in detected values fed from the load detectors arranged at the head side of the subject, wherein FIG. 11A depicts the image of the variation when the subject is in the supine position, FIG. 11B depicts the image of the variation when the subject is in the recumbent position, and FIG. 11C depicts the image of the variation when the subject is in the prone position.

FIGS. 12A, 12B, and 12C depict other exemplary schematic images of the variation in the detected values fed from the load detectors arranged at the head side of the subject, wherein FIG. 12A depicts the other exemplary image of the variation when the subject is in the supine position, FIG. 12B depicts the other exemplary image of the variation when the subject is in the recumbent position, and FIG. 12C depicts the other exemplary image of the variation when the subject is in the prone position.

EMBODIMENTS

<First Embodiment>

An embodiment of the present disclosure will be explained with reference to FIG. 1 to FIGS. 19A and 19B.

Figure 1:
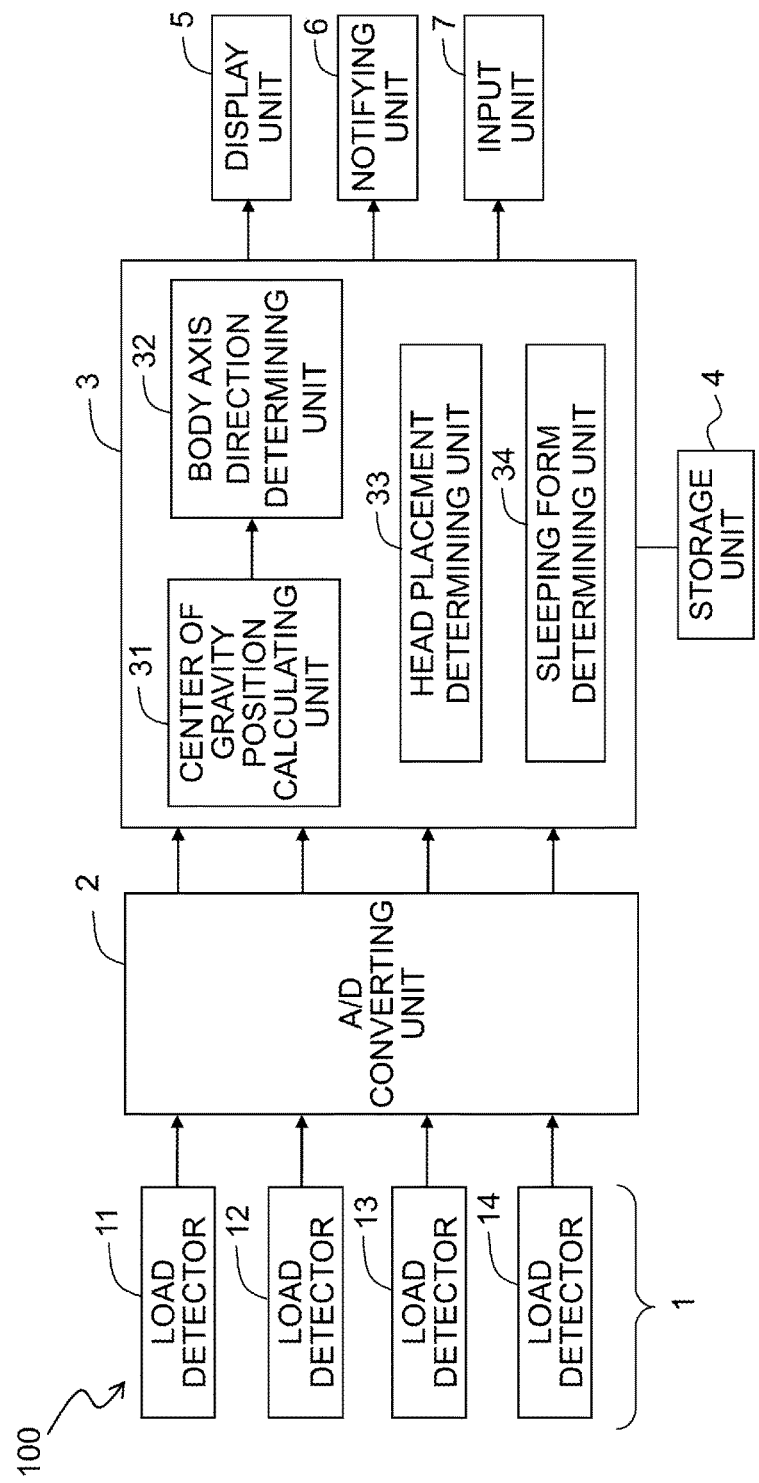
FIG. 1 is a block diagram depicting an overall configuration of a body state detecting apparatus according to an embodiment of the present disclosure.

As depicted in FIG. 1, a body state detecting apparatus 100 of this embodiment has mainly a load detecting unit 1, a control unit (a controller) 3, a storage unit (a storage, a memory) 4, and a display unit (a display) 5. The load detecting unit 1 and the control unit 3 are connected via an A/D converting unit (an A/D convertor) 2. The control unit 3 is further connected with a notifying unit 6 and an input unit 7.

The load detecting unit 1 is provided with four load detectors 11, 12, 13, 14. Each of the load detectors 11, 12, 13, 14 is a load detector which detects the load by using, for example, a beam-type load cell. Such a load detector is disclosed, for example, in Japanese Patent No. 4829020 and Japanese Patent No. 4002905. Each of the load detectors 11, 12, 13, 14 is connected to the A/D converting unit 2 by means of wiring.

The A/D converting unit 2 is provided with an A/D converter which converts the analog signal fed from the load detecting unit 1 into the digital signal. The A/D converting unit 2 is connected to each of the load detecting unit 1 and the control unit 3 by means of wiring.

The control unit 3 is an exclusive or general-purpose computer. A center of gravity position calculating unit 31, a body axis direction determining unit 32, a head placement determining unit 33, and a sleeping form determining (judging) unit 34 are constructed therein.

The storage unit 4 is a storage device which stores the data used in the body state detecting apparatus 100. For example, it is possible to use a hard disk (magnetic disk) therefor. The display unit 5 is a monitor such as a liquid crystal monitor or the like for displaying the information outputted from the control unit 3 for a user of the body state detecting apparatus 100.

The notifying unit 6 is provided with a device for visually or auditorily performing predetermined notification on the basis of the information fed from the control unit 3, for example, a speaker. The input unit 7 is an interface for performing predetermined input for the control unit 3, which may be a keyboard and a mouse.

An explanation will be made about the operation for detecting a body state of the subject (human subject) on the bed, by using the body state detecting apparatus 100 described above.

Figure 2:
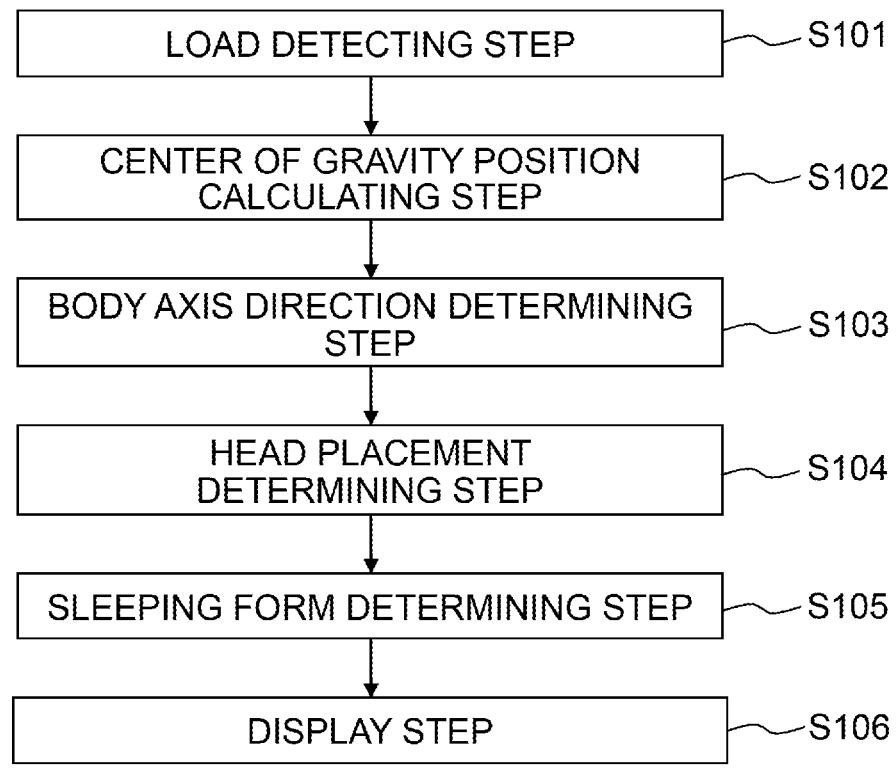
FIG. 2 is a flow chart depicting an operational flow according to the embodiment of the present disclosure.

As depicted in FIG. 2, the detection of the body state of the subject, which is based on the use of the body state detecting apparatus 100, includes a load detecting step (S101), a center of gravity position calculating step (S102), a body axis direction determining step (S103), a head placement determining step (S104), a sleeping form determining (judging) step (S105), and a display step (S106). The load detecting step (S101) is a step of detecting the load of the subject. The center of gravity position calculating step (S102) is a step of calculating the center of gravity position of the subject on the basis of the detected load. The body axis direction determining step (S103) is a step of determining the extending direction of the body axis of the subject on the basis of the acquired center of gravity position. The head placement determining step (S104) is a step of determining at which side of the center of gravity the head of the subject is placed in the body axis direction. The sleeping form determining step (S105) is a step of determining whether the subject is in a supine position, a recumbent position or a prone position. The display step (S106) is a step of displaying the body state of the subject determined in the foregoing steps.

<Load Detecting Step>

Figure 3:
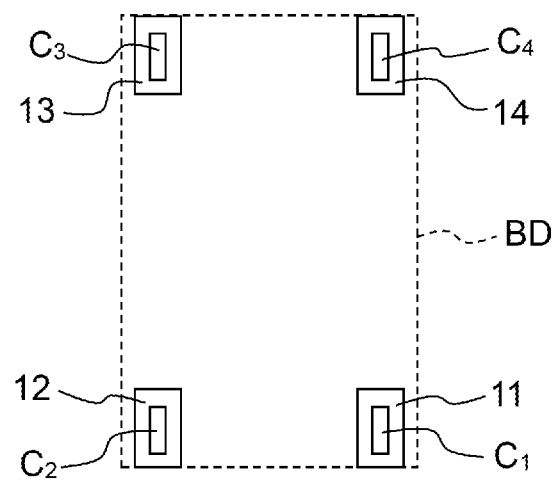
FIG. 3 is an illustrative view depicting an arrangement of load detectors with respect to a bed.

In order to perform the load detecting step S101, the four load detectors 11, 12, 13, 14 of the load detecting unit 1 are arranged under the feet (legs) of a bed to be used by the subject. Specifically, as depicted in FIG. 3, the load detectors 11, 12, 13, 14 are arranged respectively under casters $C_1$, $C_2$, $C_3$, $C_4$ attached to lower end portions of the feet disposed at the four corners of the bed BD.

Figure 4:
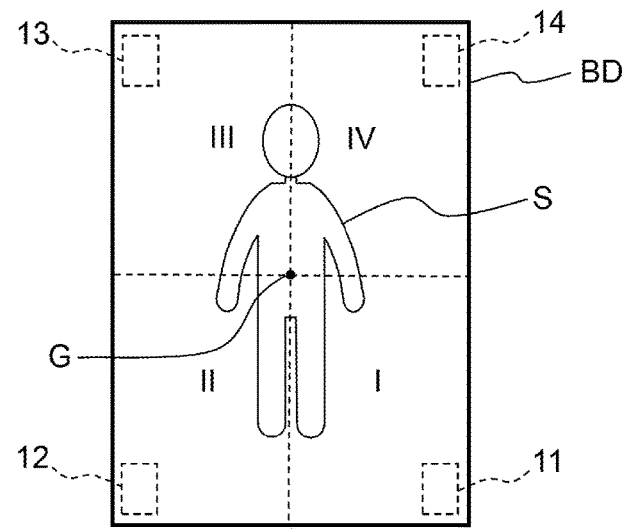
FIG. 4 is an illustrative view depicting an arrangement of four load detection areas defined on the upper surface of the bed.

When the load detectors 11, 12, 13, 14 are arranged under the casters $C_1$, $C_2$, $C_3$, $C_4$ respectively, the load, which is applied to the upper surface of the bed BD, is thereby detected in a dispersed manner by the four load detectors 11, 12, 13, 14. Specifically, as depicted in FIG. 4, the rectangular upper surface of the bed BD is longitudinally divided into two and laterally divided into two, and thus the upper surface is equally divided into four rectangular areas I to IV.

Accordingly, the load, which is applied to the area I positioned with the left lower half of the body of the subject (human subject) S lying on his/her back (face up, that is in the supine position) at the central portion of the bed BD, is principally detected by the load detector 11, and the load, which is applied to the area II positioned with the right lower half of the body of the subject S in the same state, is principally detected by the load detector 12. Similarly, the load, which is applied to the area III positioned with the right upper half of the body of the subject S lying on his/her back at the central portion of the bed BD, is principally detected by the load detector 13, and the load, which is applied to the area IV positioned with the left upper half of the body of the subject S in the same state, is principally detected by the load detector 14.

Each of the load detectors 11, 12, 13, 14 detects the load (load change), and the load (load change) is outputted as the analog signal to the A/D converting unit 2. The A/D converting unit 2 converts the analog signal into the digital signal while using the sampling period of, for example, 0.1 seconds, and the digital signal (referred to hereinafter as "load signal") is outputted to the control unit 3.

Figure 5:
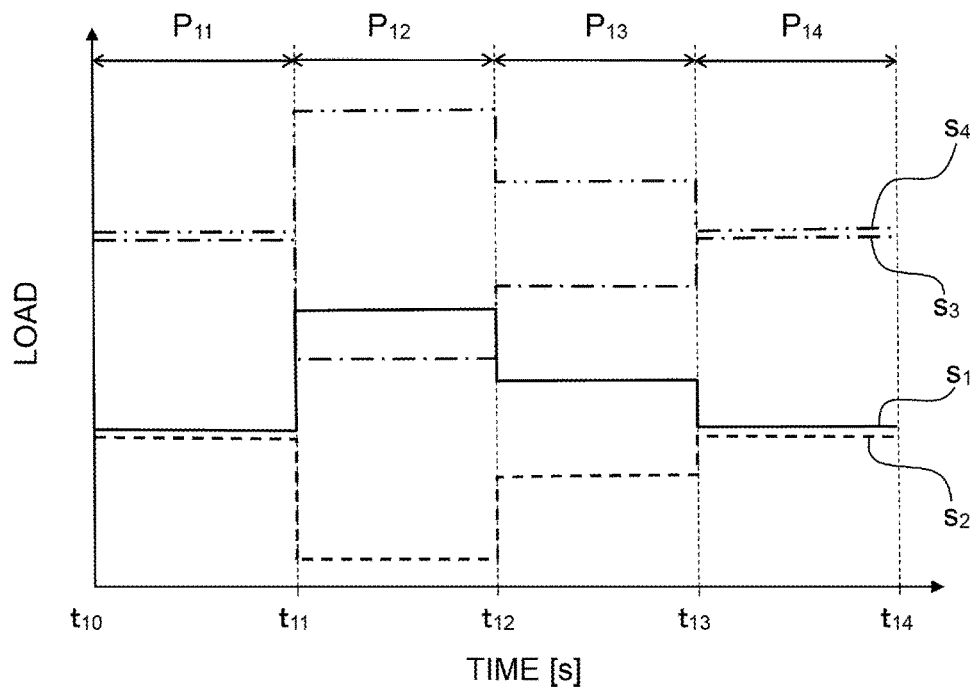
FIG. 5 depicts exemplary load signals fed from the load detectors.

Exemplary load signals are depicted in FIG. 5. FIG. 5 depicts the load signals $s_1$ (solid line), $s_2$ (broken line), $s_3$ (alternate long and short dash line), and $s_4$ (alternate long and two short dashes line) fed from the load detectors 11, 12, 13, 14 as outputted during the period ranging from the time $t_{10}$ to the time $t_{14}$. The following fact has been observed. That is, the subject S lay on his/her back at the central portion of the bed BD during the period ranging from the time $t_{10}$ to the time $t_{11}$ (period $P_{11}$) as depicted in FIG. 4. The subject S moved to the side of the areas I, IV of the bed BD during the period ranging from the time $t_{11}$ to the time $t_{12}$ (period $P_{12}$). The subject S moved to some extent to the central side of the bed BD during the period ranging from the time $t_{12}$ to the time $t_{13}$ (period $P_{13}$) as compared with the period $P_{12}$. The subject S lay on his/her back at the central portion of the bed BD during the period ranging from the time $t_{13}$ to the time $t_{14}$ (period $P_{14}$).

The subject S lay on his/her back at the central portion of the bed BD as depicted in FIG. 4 during the period $P_{11}$. Therefore, the signals $s_3$, $s_4$, which are fed from the load detectors 13, 14 arranged on the head side of the subject S, are approximately equal to one another during the period $P_{11}$, and the signals $s_1$, $s_2$, which are fed from the load detectors 11, 12 arranged on the foot side (leg side) of the subject S, are approximately equal to one another.

The subject S moved to the side of the areas I, IV of the bed BD during the period $P_{12}$. Therefore, during the period $P_{12}$, the signals $s_1$, $s_4$, which are fed from the load detectors 11, 14 arranged in the areas I, IV, exhibit the large load values as compared with the period $P_{11}$, and the signals $s_2$, $s_3$, which are fed from the load detectors 12, 13 arranged in the areas II, III, exhibit the small load values as compared with the period $P_{11}$.

The subject S moved to some extent to the central side of the bed BD during the period $P_{13}$ as compared with the period $P_{12}$. Therefore, during the period $P_{13}$, the signals $s_1$, $s_4$, which are fed from the load detectors 11, 14 arranged in the areas I, IV, exhibit the small load values as compared with the period $P_{12}$, and the signals $s_2$, $s_3$, which are fed from the load detectors 12, 13 arranged in the areas II, III, exhibit the large load values as compared with the period $P_{12}$.

The subject S lay on his/her back at the central portion of the bed BD during the period $P_{14}$ in the same manner as the period $P_{11}$. Therefore, the signals $s_1$ to $s_4$, which are provided during the period $P_{14}$, are the same as the signals $s_1$ to $s_4$ provided during the period $P_{11}$.

<Center of Gravity Position Calculating Step>

Figure 6:
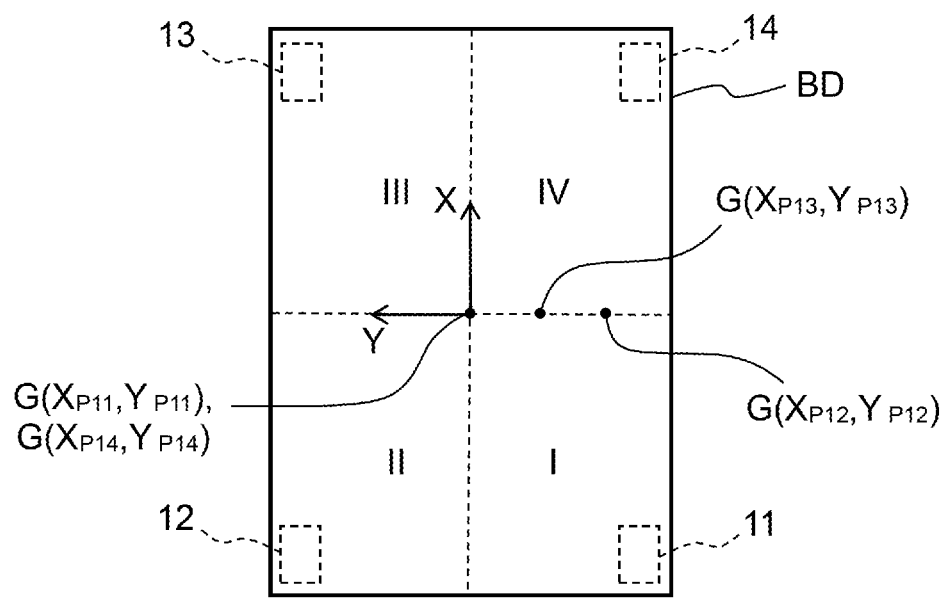
FIG. 6 is an illustrative view depicting a movement of the center of gravity position of a subject on the bed.

In the center of gravity position calculating step S102, the center of gravity position calculating unit 31 periodically calculates the position G (X, Y) of the center of gravity G of the subject S on the bed BD at a time t with a predetermined period T (for example, a period equal to the sampling period of 0.1 seconds described above) on the basis of the load signals $s_1$ to $s_4$ fed from the load detectors 11 to 14. In this case, (X, Y) indicates the coordinates on the XY coordinate plane in which X extends in the longitudinal direction (long side direction) of the bed BD and Y extends in the lateral direction (short side direction) of the bed BD while the central portion of the bed BD is the origin (FIG. 6).

The calculation of the position G (X, Y) of the center of gravity G by the center of gravity position calculating unit 31 is performed in accordance with the following operation. That is, G (X, Y) is calculated in accordance with the following formulas assuming that the coordinates of the load detectors 11, 12, 13, 14 are $(X_{11}, Y_{11})$, $(X_{12}, Y_{12})$, $(X_{13}, Y_{13})$, and $(X_{14}, Y_{14})$ respectively, and the detected load values of the load detectors 11, 12, 13, 14 are $W_{11}$, $W_{12}$, $W_{13}$, and $W_{14}$ respectively.

$$X = \frac{X_{11} \times W_{11} + X_{12} \times W_{12} + X_{13} \times W_{13} + X_{14} \times W_{14}}{W_{11} + W_{12} + W_{13} + W_{14}} \quad \text{Formula 1}$$

$$Y = \frac{Y_{11} \times W_{11} + Y_{12} \times W_{12} + Y_{13} \times W_{13} + Y_{14} \times W_{14}}{W_{11} + W_{12} + W_{13} + W_{14}} \quad \text{Formula 2}$$

An example of position G (X, Y) of the center of gravity G calculated by the center of gravity position calculating unit 31 is depicted in FIG. 6. FIG. 6 depicts the positions G $(X_{P11}, Y_{P11})$, G $(X_{P12}, Y_{P12})$, G $(X_{P13}, Y_{P13})$, G $(X_{P14}, Y_{P14})$ of the center of gravity G of the subject S on the bed BD at the times $t_{110}$, $t_{120}$, $t_{130}$, $t_{140}$ included in the periods $P_{11}$, $P_{12}$, $P_{13}$, $P_{14}$ depicted in FIG. 5 respectively. The center of gravity position calculating unit 31 causes the storage unit 4, for example, to store the position G (X, Y) of the center of gravity G at each time t as acquired in the above manner.

<Body Axis Direction Determining Step>

In the body axis direction determining step S103, the body axis direction determining unit 32 determines the extending direction of the body axis SA of the subject S under such a principle as below, by using the position G (X, Y) of the center of gravity G calculated in the center of gravity position calculating step S102.

The respiration of human is performed by moving the chest and the diaphragm to expand and shrink the lungs. In this context, when the air is inhaled, i.e., when the lungs are expanded, the diaphragm is lowered downwardly, and the internal organs are also moved downwardly. On the other hand, when the air is expired, i.e., when the lungs are shrunk, the diaphragm is raised upwardly, and the internal organs are also moved upwardly. As a result of the research performed by the inventors of the present invention, it has been found out that the center of gravity G slightly moves in accordance with the movement of the internal organs, and the movement of the center of gravity G occurs approximately along the extending direction of the backbone (body axis direction).

Therefore, the body axis direction determining unit 32 can determine the extending direction of the body axis SA of the subject S by acquiring the direction of a minute movement of the center of gravity G calculated by the center of gravity position calculating unit 31.

Specifically, for example, first, the body axis direction determining unit 32 takes out the position G $(X_{t20}, Y_{t20})$ of the center of gravity G of the subject S at the time $t_{20}$ stored in the storage unit 4 in the center of gravity position calculating step S102 (FIG. 7A), the position G $(X_{t21}, Y_{t21})$ of the center of gravity G of the subject S at the time $t_{21}$ at which a little time has passed since the time $t_{20}$ (for example, one second after the time $t_{20}$) (FIG. 7B), and the position G $(X_{t22}, Y_{t22})$ of the center of gravity G of the subject S at the time $t_{22}$ at which a little time has passed since the time $t_{21}$ (for example, one second after the time $t_{21}$) (FIG. 7C). Then, the body axis direction determining unit 32 determines the extending direction of the body axis SA by acquiring the straight line passing through those positions G (FIG. 7D).

As described above, the center of gravity G of the subject S moves along the extending direction of the body axis SA of the subject S in accordance with the respiration of the subject S. Therefore, as described above, the body axis direction determining unit 32 can determine the extending direction of the body axis SA on the basis of the position G (X, Y) of a plurality of centers of gravity G included in the time corresponding to one respiration, in other words, a plurality of center of gravity positions G (X, Y) obtained by using a shorter sampling period than the period of one respiration (about 3 to 5 seconds).

<Head Placement Determining Step>

In the head placement determining step S104, the head placement determining unit 33 acquires a placement of the head of the subject S under such a principle as below, by using the load signals $s_1$ to $s_4$ fed from the load detecting unit 1 and the extending direction of the body axis SA determined in the body axis direction determining step S103.

Figure 8A:
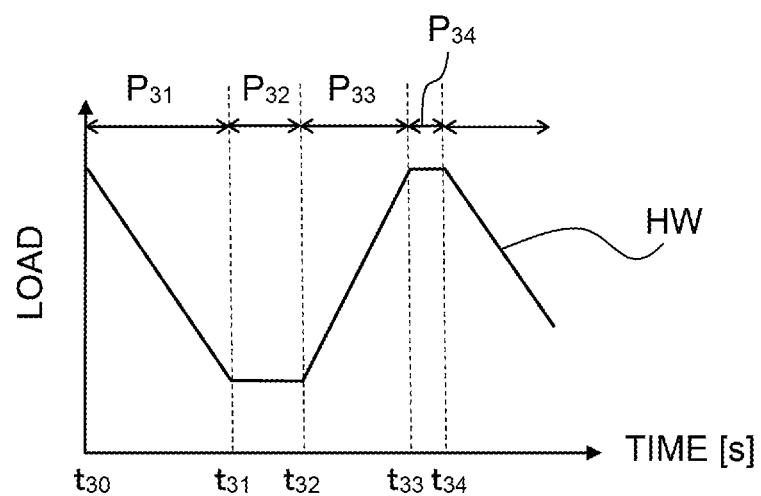
Figure 8B:
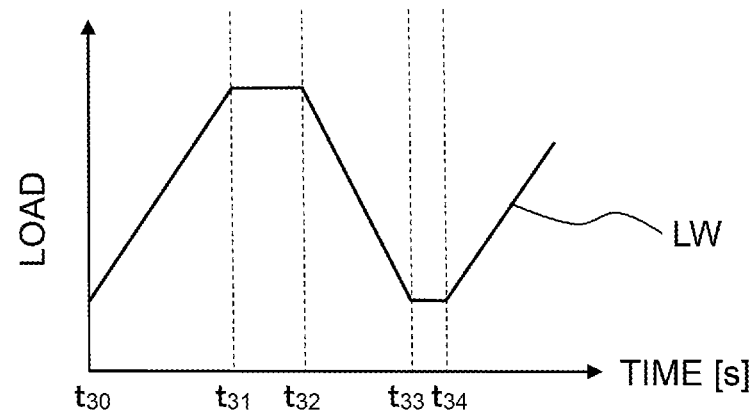
Figure 9A:
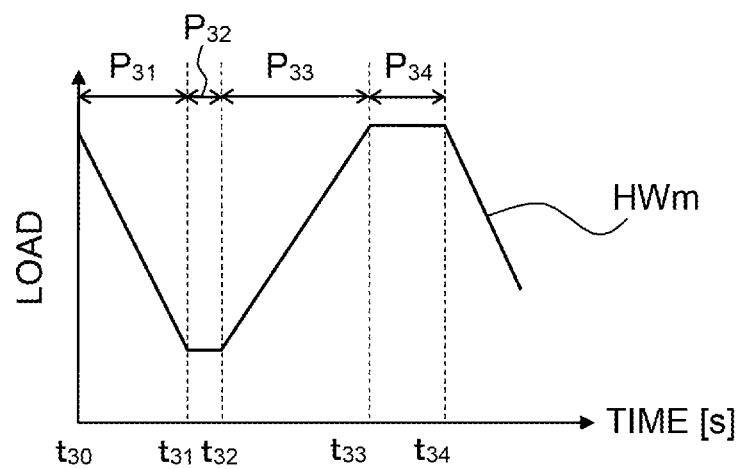
Figure 9B:
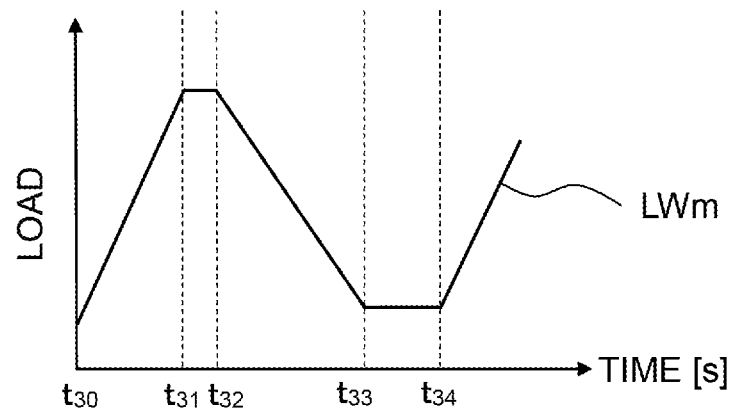

According to a research performed by the inventors of the present invention about how the respiration of the subject S on the bed BD affects the load signals fed from the load detectors, it is known that the load signals fed from the load detectors positioned at the head side of the subject S (corresponding to the load detectors 13, 14 in the situation depicted in FIG. 4), and the load signals fed from the load detectors positioned at the feet side (leg side) of the subject S (corresponding to the load detectors 11, 12 in the situation depicted in FIG. 4) vary so as to present such waveforms as depicted respectively in FIGS. 8A and 8B.

FIG. 8A depicts a waveform of the load signal fed from a load detector positioned at the head side of the subject S (hereinafter, referred to as "head-side waveform HW"). FIG. 8B depicts a waveform of the load signal fed from a load detector positioned at the feet side (leg side) of the subject S (hereinafter, referred to as "feet-side waveform (leg side waveform) LW"). The time $t_{30}$ is for the subject S to start an inhalation, the time $t_{31}$ is for the subject S to end the inhalation, the time $t_{32}$ is for the subject S to start an expiration, the time $t_{33}$ is for the subject S to end the expiration, and the time $t_{34}$ is for the subject S to start the next inhalation.

Just as depicted in FIGS. 8A and 8B, during the period from the time $t_{30}$ to the time $t_{31}$ (the inhalation period $P_{31}$) when the subject S is in inhalation, there is a gradual decrease in the detected value by the load detector arranged at the head side of the subject S, while there is a gradual increase in the detected value by the load detector arranged at the feet side of the subject S. This is because the center of gravity position G of the subject S moves to the feet side when in the inhalation.

During the period from the time $t_{32}$ to the time $t_{33}$ (the expiration period $P_{33}$) when the subject S is in expiration, there is a gradual increase in the detected value by the load detector arranged at the head side of the subject S, while there is a gradual decrease in the detected value by the load detector arranged at the feet side of the subject S. This is because the center of gravity position G of the subject S moves to the head side when in the expiration.

According to the perception (findings, observation) of the inventors, the head-side waveform HW and the feet-side waveform LW depicted in FIGS. 8A and 8B have the following features.

First, in both the head-side waveform HW and the feet-side waveform LW, the inhalation period $P_{31}$ during which the subject S is in inhalation is longer than the expiration period $P_{33}$ during which the subject S is in expiration. That is, in the head-side waveform HW, the falling inclination of the waveform during the inhalation period $P_{31}$ is less steep than the rising inclination of the waveform during the expiration period $P_{33}$ whereas in the feet-side waveform LW, the rising inclination of the waveform during the inhalation period $P_{31}$ is less steep than the falling inclination of the waveform during the expiration period $P_{33}$.

Further, in both the head-side waveform HW and the feet-side waveform LW, there are a post-inhalation hold period $P_{32}$ from the time $t_{31}$ for the subject S to end the inhalation to the time $t_{32}$ for the subject S to start the expiration, and a post-expiration hold period $P_{34}$ from the time $t_{33}$ for the subject S to end the expiration to the time $t_{34}$ for the subject S to start the next inhalation. During those hold periods $P_{32}$, $P_{34}$, an approximately flat part appears in the vicinity of the peak of the waveform. Then, the post-inhalation hold period $P_{32}$ is longer than the post-expiration hold period $P_{34}$.

The head-side waveform HW and the feet-side waveform LW have the above features respectively, and the chevron waveform or the notch waveform representing the inhalation period $P_{31}$, the post-inhalation hold period $P_{32}$ and the expiration period $P_{33}$ is an asymmetrical waveform along the time axis with respect to the center of the post-inhalation hold period $P_{32}$ (between the front and the rear of the center). Further, if a comparison is made between the head-side waveform HW and the feet-side waveform LW, then in the rising part of the waveform, the rising inclination is steeper in the head-side waveform HW than in the feet-side waveform LW, while the approximately flat part following the rising of the waveform is shorter in the head-side waveform HW than in the feet-side waveform LW. On the other hand, in the falling part of the waveform, the falling inclination is less steep in the head-side waveform HW than in the feet-side waveform LW, while the approximately flat part following the falling of the waveform is longer in the head-side waveform HW than in the feet-side waveform LW.

Therefore, the head placement determining unit 33 can analyze a load signal fed from the load detecting unit 1 so as to determine (judge), based on at least one of the inhalation period $P_{31}$, the post-inhalation hold period $P_{32}$, the expiration period $P_{33}$, and the post-expiration hold period $P_{34}$, whether the load signal exhibits the head-side waveform HW or the feet-side waveform LW. Then, based on that determination (judgement), the head placement determining unit 33 can determine whether the head of the subject S is placed or the feet of the subject S is placed, in the position on the bed BD corresponding to that load signal.

Further, the inventors of the present invention have further investigated the shapes of the head-side waveforms and the feet-side waveforms of a plurality of subjects, and discovered that some of subjects exhibit a head-side waveform and a feet-side waveform having different features from those of the above head-side waveform HW and feet-side waveform LW. A head-side waveform HWm (FIG. 9A) and a feet-side waveform LWm (FIG. 9B) exhibited by such a subject S have the following features.

First, in both the head-side waveform HWm and the feet-side waveform LWm, the inhalation period $P_{31}$ during which the subject S is in inhalation is shorter than the expiration period $P_{33}$ during which the subject S is in expiration. That is, in the head-side waveform HWm, the falling inclination of the waveform during the inhalation period $P_{31}$ is steeper than the rising inclination of the waveform during the expiration period $P_{33}$ whereas in the feet-side waveform LWm, the rising inclination of the waveform during the inhalation period $P_{31}$ is steeper than the falling inclination of the waveform during the expiration period $P_{33}$.

Further, in both the head-side waveform HWm and the feet-side waveform LWm, there are a post-inhalation hold period $P_{32}$ from the time $t_{31}$ for the subject S to end the inhalation to the time $t_{32}$ for the subject S to start the expiration, and a post-expiration hold period $P_{34}$ from the time $t_{33}$ for the subject S to end the expiration to the time $t_{34}$ for the subject S to start the next inhalation. During those hold periods $P_{32}$, $P_{34}$, an approximately flat part appears in the vicinity of the peak of the waveform. Then, the post-inhalation hold period $P_{32}$ is shorter than the post-expiration hold period $P_{34}$.

The head-side waveform HWm and the feet-side waveform LWm have the above features respectively, and the chevron waveform or the notch waveform representing the inhalation period $P_{31}$, the post-inhalation hold period $P_{32}$ and the expiration period $P_{33}$ is an asymmetrical waveform along the time axis with respect to the center of the post-inhalation hold period $P_{32}$ (halfway between the time $t_{31}$ and the time $t_{32}$). Further, if a comparison is made between the head-side waveform HWm and the feet-side waveform LWm, then in the rising part of the waveform, the rising inclination is less steep in the head-side waveform HWm than in the feet-side waveform LWm, while the approximately flat part following the rising of the waveform is longer in the head-side waveform HWm than in the feet-side waveform LWm. On the other hand, in the falling part of the waveform, the falling inclination is steeper in the head-side waveform HWm than in the feet-side waveform LWm, while the approximately flat part following the falling of the waveform is shorter in the head-side waveform HWm than in the feet-side waveform LWm.

In the case where the subject S exhibits such head-side waveform HWm and the feet-side waveform LWm, the head placement determining unit 33 can also analyze a load signal fed from the load detecting unit 1 so as to determine, based on at least one of the inhalation period $P_{31}$, the post-inhalation hold period $P_{32}$, the expiration period $P_{33}$, and the post-expiration hold period $P_{34}$, whether the load signal exhibits the head-side waveform HWm or the feet-side waveform LWm. Then, based on that determination, the head placement determining unit 33 can determine whether the head of the subject S is placed or the feet of the subject S is placed, in the position on the bed BD corresponding to that load signal. Note that it is preferable to store the information on whether the subject S exhibits the head-side waveform HW and the feet-side waveform LW or the head-side waveform HWm and the feet-side waveform LWm, for example, in storage unit 4 previously.

Next, an example of a specific procedure for the head placement determining unit 33 to determine the head placement of the subject S will be explained. The explanation will be made using, as an example, a procedure performed after it is determined that the body axis SA extends across the area II and the area IV in the body axis direction determining step S103 (FIG. 7D). Here, the subject S is supposed to exhibit the head-side waveform HW (FIG. 8A) and the feet-side waveform LW (FIG. 8B).

In this case, it is conceivable that the head of the subject S is placed in either the area II or the area IV. Therefore, the head placement determining unit 33 determines the head placement based on the load signal $s_2$ fed from the load detector 12 measuring mainly the load applied on the area II, or the load signal $s_4$ fed from the load detector 14 measuring mainly the load applied on the area IV. Because the step remains substantially the same no matter which load signal is used, the head placement determining unit 33 may arbitrarily select one or use both but, here, the head placement determining unit 33 is supposed to use the load signal $s_4$ fed from the load detector 14.

Having selected the load signal $s_4$, the head placement determining unit 33 then takes out, from the load signal $s_4$, a minute oscillation of the detected value (a respiratory signal or respiration waveform) caused by the movement of the center of gravity due to the respiration. This is because the load signal $s_4$ includes the static load due to the body weight of the subject S, and the load signal caused by the movement of the center of gravity due to the respiration of the subject S. It is known that the human being performs about 12 to 20 respirations per minute. This is about 3 seconds to 5 seconds when converted into period, or about 0.2 Hz to 0.33 Hz when converted into frequency. Hence, the head placement determining unit 33 performs, for example, Fourier transform, frequency filter process, and/or inverse Fourier transform for the load signal $s_4$ fed from the load detector 14, and takes out the respiration waveform with the frequency ranging from about 0.2 Hz to about 0.33 Hz.

Figure 10A:
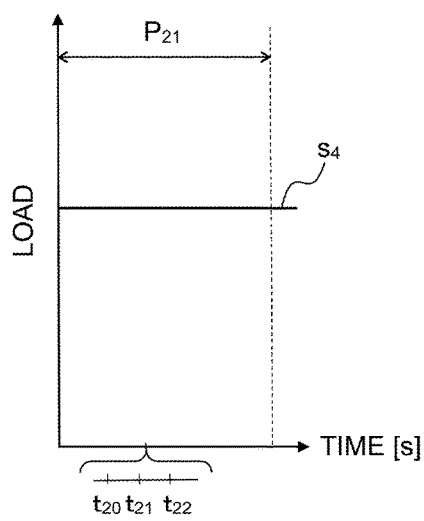
FIG. 10A depicts an exemplary load signal fed from the load detector.
Figure 10B:
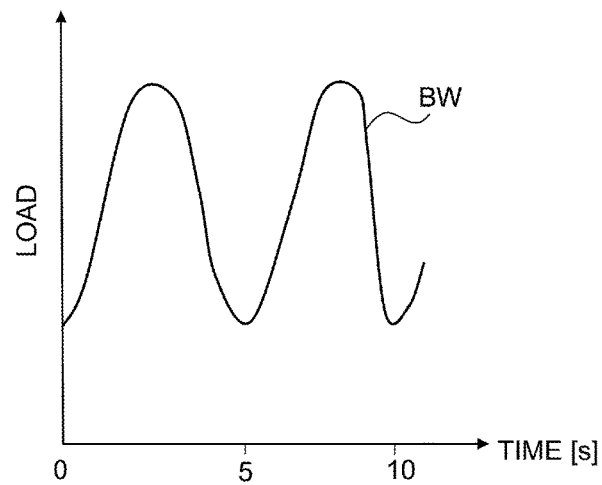
FIG. 10B depicts an exemplary respiration waveform taken out from the load signal of FIG. 10A.

FIG. 10A depicts the load signal $s_4$ fed from the load detector 14 during the period $P_{21}$, and FIG. 10B depicts the respiration waveform (respiratory signal) BW taken out from the load signal $s_4$ of FIG. 10A. The period $P_{21}$ depicted in FIG. 10A includes the time $t_{20}$ to the time $t_{22}$ depicted in FIGS. 7A to 7D. In this period, as described earlier on, the subject S is almost static in the supine position with the body axis SA extending across the area II and the area IV. Further, because a far smaller variation in load value occurs with the movement of the center of gravity G caused by the respiration, compared to the scale of the static load due to the body weight of the subject S, FIG. 10A does not show the respiration waveform BW.

FIG. 10B depicts the respiration waveform BW during a period corresponding to any ten seconds in the period $P_{21}$. Because only the variation in load value occurring with the movement of the center of gravity G caused by the respiration is taken out, FIG. 10B explicitly shows the minute variation in load value occurring with the movement of the center of gravity G.

The head placement determining unit 33 then analyzes the respiration waveform BW taken out and, based on the fact that the inhalation period $P_{31}$ is longer than the expiration period $P_{33}$, identifies the position, in the waveform BW, corresponding to the inhalation period $P_{31}$. Then, if the respiration waveform BW falls in that identified position, then the respiration waveform BW is the head-side waveform HW, thereby determining that the head of the subject S is present in the area IV. On the contrary, if the respiration waveform BW rises in that identified position, then the respiration waveform BW is the feet-side waveform LW, thereby determining that the head of the subject S is present in the area II.

Note that, when the subject S exhibits the head-side waveform HWm (FIG. 9A) and the feet-side waveform LWm (FIG. 9B), it is also possible to determine the head placement of the subject S by the same procedure as described above.

<Sleeping Form Determining Step>

In the sleeping form determining (judging) step S105, the sleeping form determining (judging) unit 34 determines whether a sleeping form of the subject S is the supine position, the recumbent position, or the prone position, under such a principle as below, by using the load signals $s_1$ to $s_4$ fed from the load detecting unit 1.

After the inventors of the present invention had observed the load signals fed from the load detecting unit 1 representing the respiration of the subject S on the bed BD in various sleeping forms of the subject S, it was known, as depicted in FIGS. 11A to 11C and FIGS. 12A to 12C, that the load signals differ with diverse sleeping forms such as in the supine, recumbent and prone positions.

Figure 11A:
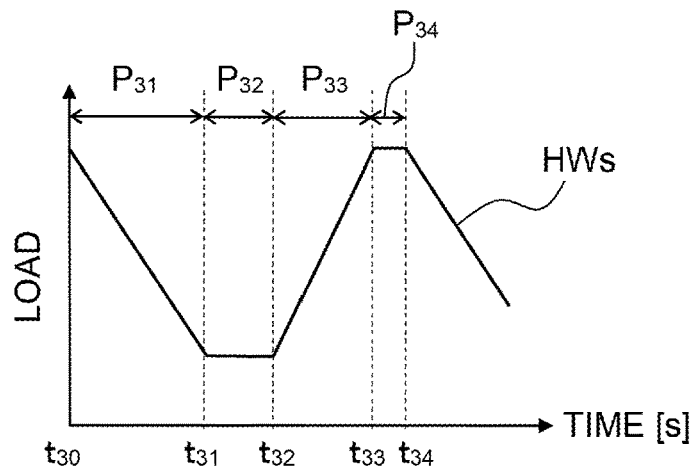
Figure 11B:
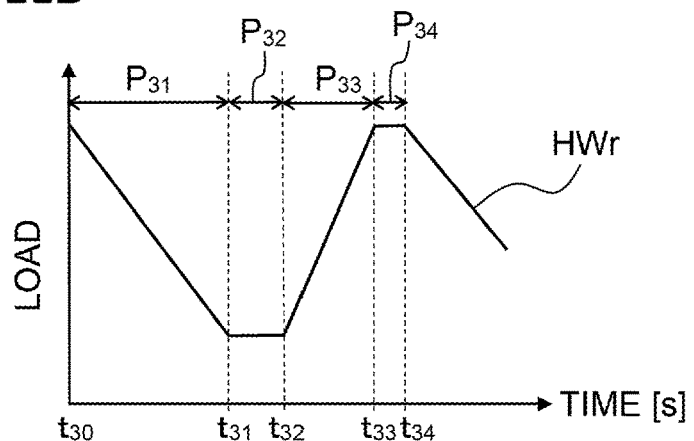
Figure 11C:
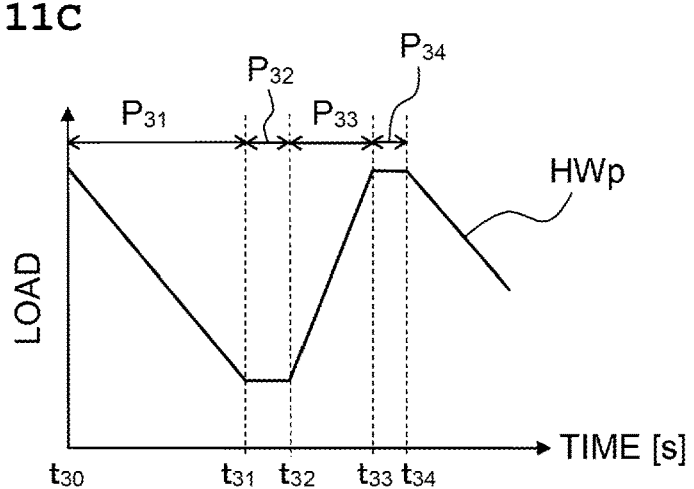
Figure 12A:
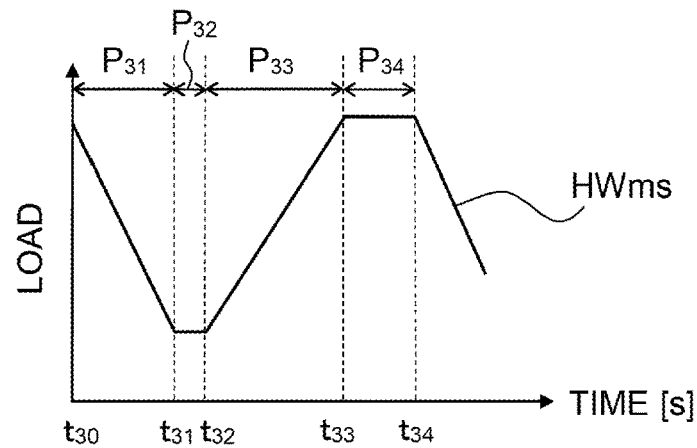
Figure 12B:
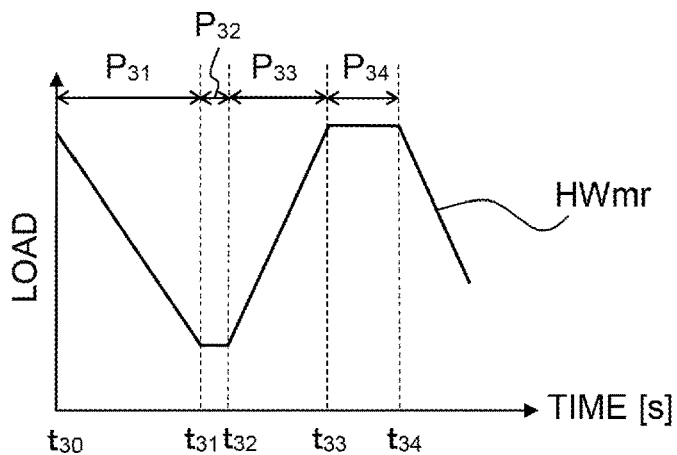
Figure 12C:
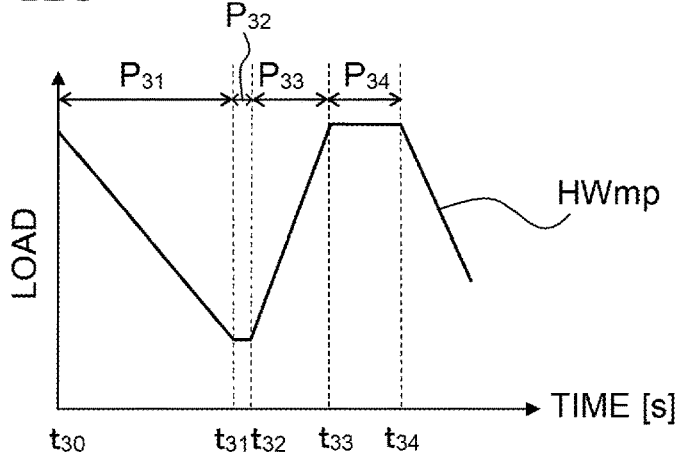

Each of FIGS. 11A to 11C and FIGS. 12A to 12C depicts the head-side waveform of the subject S. Waveforms HWs and HWms in FIGS. 11A and 12A depict the head-side waveforms of the subject S in the supine position. Waveforms HWr and HWmr in FIGS. 11B and 12B depict the head-side waveforms of the subject S in the recumbent position. Waveforms HWp and HWmp in FIGS. 11C and 12C depict the head-side waveforms of the subject S in the prone position.

According to an analysis of those waveforms, the waveforms depicted in FIGS. 11A to 12C have the following features, respectively. The waveforms HWs (FIG. 11A) and HWms (FIG. 12A) obtained when the subject S in the supine position are the same as the head-side waveforms HW and HWm depicted respectively in FIGS. 8A and 9A, and have the features explained in the relation with FIGS. 8A and 9A.

In the waveform HWp (FIG. 11C) and the waveform HWmp (FIG. 12C) obtained when the subject S is in the prone position, the inhalation period $P_{31}$ is longer than the inhalation period $P_{31}$ of the waveforms HWs and HWms, the post-inhalation hold period $P_{32}$ is shorter than the post-inhalation hold period $P_{32}$ of the waveforms HWs and HWms, and the expiration period $P_{33}$ is shorter than the expiration period $P_{33}$ of the waveforms HWs and HWms. In other words, compared with the waveforms HWs and HWms, the waveforms HWp and HWmp have such a shape that peaks on the notch side is shifted in the positive direction on the time axis. Therefore, the falling inclination during the inhalation period $P_{31}$ in the waveforms HWp and HWmp is less steep than the falling inclination during the inhalation period $P_{31}$ in the waveforms HWs and HWms, while the rising inclination during the expiration period $P_{33}$ in the waveforms HWp and HWmp is steeper than the rising inclination during the expiration period $P_{33}$ in the waveforms HWs and HWms. It is understood that such a change in the waveforms is caused by the following reason. That is, when the subject S is in the prone position, his/her chest is pressed against the bed surface due to its own weight, and thus, a load is acted on the motion for inhalation such that the inhalation speed becomes slow.

The waveform HWr (FIG. 11B) and the waveform HWmr (FIG. 12B), obtained when the subject S is in the recumbent position, have an intermediate shape between the aforementioned waveform HWs and waveform HWp, and an intermediate shape between the aforementioned waveform HWms and waveform HWmp, respectively. That is, the inhalation period $P_{31}$ is longer than the inhalation period $P_{31}$ of the waveforms HWs and HWms but shorter than the inhalation period $P_{31}$ of the waveforms HWp and HWmp. Further, the post-inhalation hold period $P_{32}$ is shorter than the post-inhalation hold period $P_{32}$ of the waveforms HWs and HWms but longer than the post-inhalation hold period $P_{32}$ of the waveforms HWp and HWmp. Further, the expiration period $P_{33}$ is shorter than the expiration period $P_{33}$ of the waveforms HWs and HWms but longer than the expiration period $P_{33}$ of the waveforms HWp and HWmp.

Note that, in all of the waveforms HWs for the supine position, the waveform HWr for the recumbent position, and the waveform HWp for the prone position, the post-expiration hold period $P_{34}$ is shorter than the post-inhalation hold period $P_{32}$. On the other hand, in all of the waveform HWms for the supine position, the waveform HWmr for the recumbent position, and the waveform HWmp for the prone position, the post-expiration hold period $P_{34}$ is longer than the post-inhalation hold period $P_{32}$. Further, the above change in the waveforms similarly occurs in the feet-side waveforms LW and LWm.

Based on such a specificity of the waveforms of the sleeping form, the sleeping form determining unit 34 can analyze the respiration waveform BW included in the load signals $s_1$ to $s_4$ fed from the load detecting unit 1, so as to determine the sleeping form of the subject S based on the length of the inhalation period $P_{31}$, the length of the post-inhalation hold period $P_{32}$, the length of the expiration period $P_{33}$, and the like.

Next, an explanation will be made on a specific procedure for the sleeping form determining unit 34 to determine the sleeping form of the subject S.

The sleeping form determining unit 34 receives the respiration waveform BW (FIG. 10B) acquired by the head placement determining unit 33, further analyzes the same, and acquires the length of the inhalation period $P_{31}$. Then, if the inhalation period $P_{31}$ is shorter than a predetermined value stored beforehand, then the subject S is determined as in the supine position; if the inhalation period $P_{31}$ is almost equal to the predetermined value stored beforehand, then the subject S is determined as in the recumbent position; and if the inhalation period $P_{31}$ is longer than the predetermined value stored beforehand, then the subject S is determined as in the prone position.

<Display Step>

An undepicted image processing unit in the control unit 3 converts the information obtained by the body axis direction determining unit 32, the head placement determining unit 33 and the sleeping form determining unit 34 into an image formation signal, and sends the same out to the display unit 5. The display unit 5 visually displays the body state information received from the control unit 3 (the image processing unit) (S106).

Figure 13:
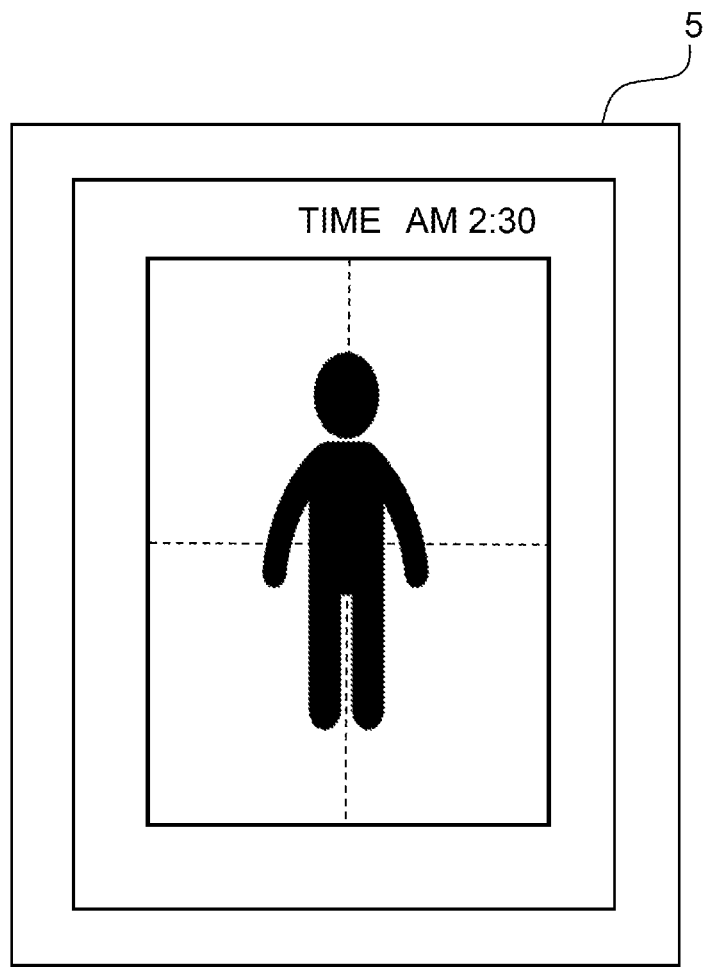
FIG. 13 depicts an example of information displayed on a display unit.

As depicted in FIG. 13, the body posture of the subject S is displayed with an image on the monitor of the display unit 5. Therefore, the user can intuitively grasp the body state of the subject S by only watching the display unit 5. Further, with the storage unit 4, the user can video-record the temporal change of the image of the body state of the subject S.

For diagnosis of sleep apnea syndrome (SAS), although overnight video-recording of the body state (body position and body posture) of sleeping patients is also performed with patients staying in a medical institution, many patients exhibit a certain disinclination against the video-recording of their sleeping forms and/or sleeping faces. However, by using the display unit 5 of the present disclosure, no sleeping face will be video-recorded and the sleeping form is recorded as a silhouette at a high anonymity such that it is possible to provide more patients with the opportunity for the diagnosis. Further, while sleeping in the prone position is recommended for SAS treatment, when the subject is in sleep, it is not possible for the subject to grasp how much time he/she could keep sleeping in the prone position. By using the present disclosure, however, because it is possible to visualize the sleeping form during the subject's sleeping, the subject is motivated to keep on training for keeping the prone position sleep.

The user can also set the system to cause the notifying unit 6 to notify the user if the subject S comes into a predetermined state. For example, it is possible for the user to set the system such that if the subject S has kept the prone position over a predetermined period of time, it is notified.

A summarization will be made below on the effects of the body state detecting apparatus 100 and the body state detecting method of the embodiment.

The body state detecting apparatus 100 and the body state detecting method of the embodiment determine the direction of the body axis SA of the subject S on the basis of a minute movement of the center of gravity G. Further, the body state detecting apparatus 100 and the body state detecting method of the embodiment determine the head placement of the subject S and determine the sleeping form (in the supine position, recumbent position, or prone position) on the basis of the variation in the load signals (respiration waveforms, respiratory signals) caused by the minute movement of the center of gravity G. Therefore, the body state detecting apparatus 100 and the body state detecting method of the embodiment can satisfactory detect the body state of the subject S without using any imaging device, expiratory detecting device and the like and without placing any burden on the subject S, only on the basis of the detecting of the load performed by the load detecting unit 1.

The body state detecting apparatus 100 and the body state detecting method of the embodiment can detect the body state of the subject S only on the basis of detecting of the load just as described above, can display the detected body state of the subject S graphically and, furthermore, can video-record the temporal change in the body state. Therefore, for the patients who exhibit the disinclination against video-recording their sleeping appearances, it is possible to provide them with the opportunity of appropriate diagnosis and treatment without bringing on the disinclination.

<Modified Embodiment>

A modification of the above embodiment will be explained as a modified embodiment of detecting the body state of the subject S.

Figure 14A:
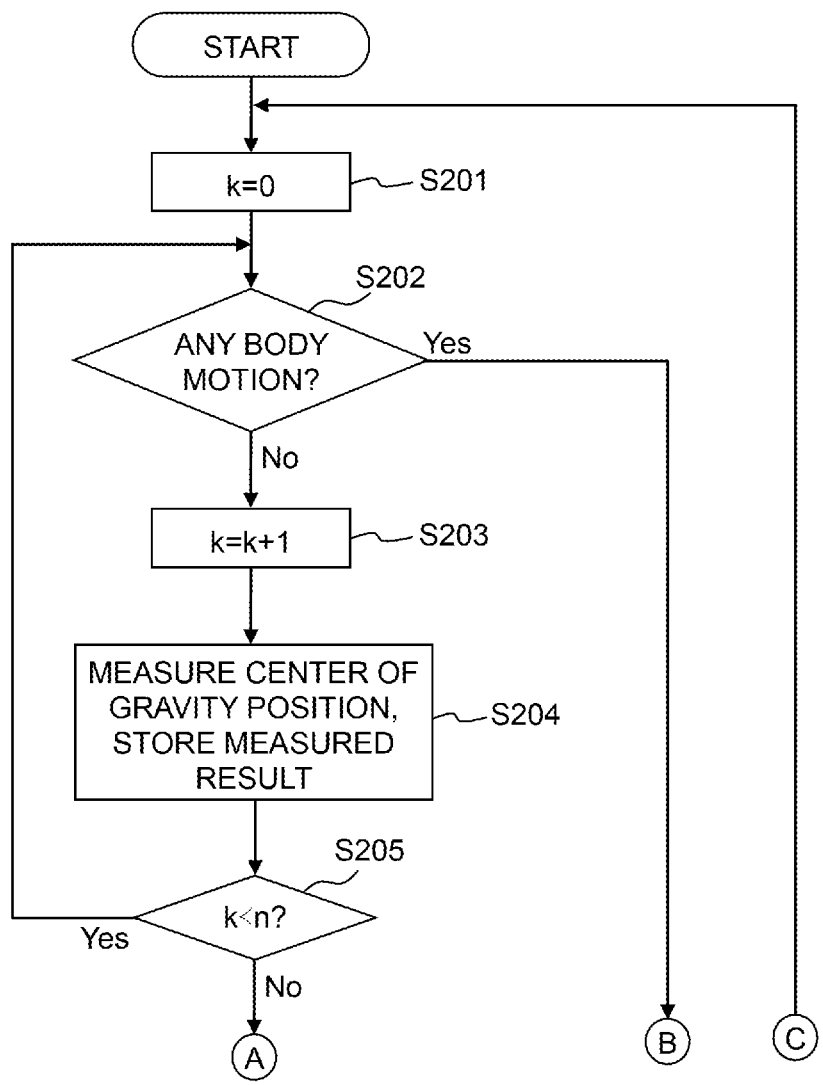
FIGS. 14A and 14B show a flow chart depicting an operational flow according to a modified embodiment of the present disclosure.
Figure 14B:
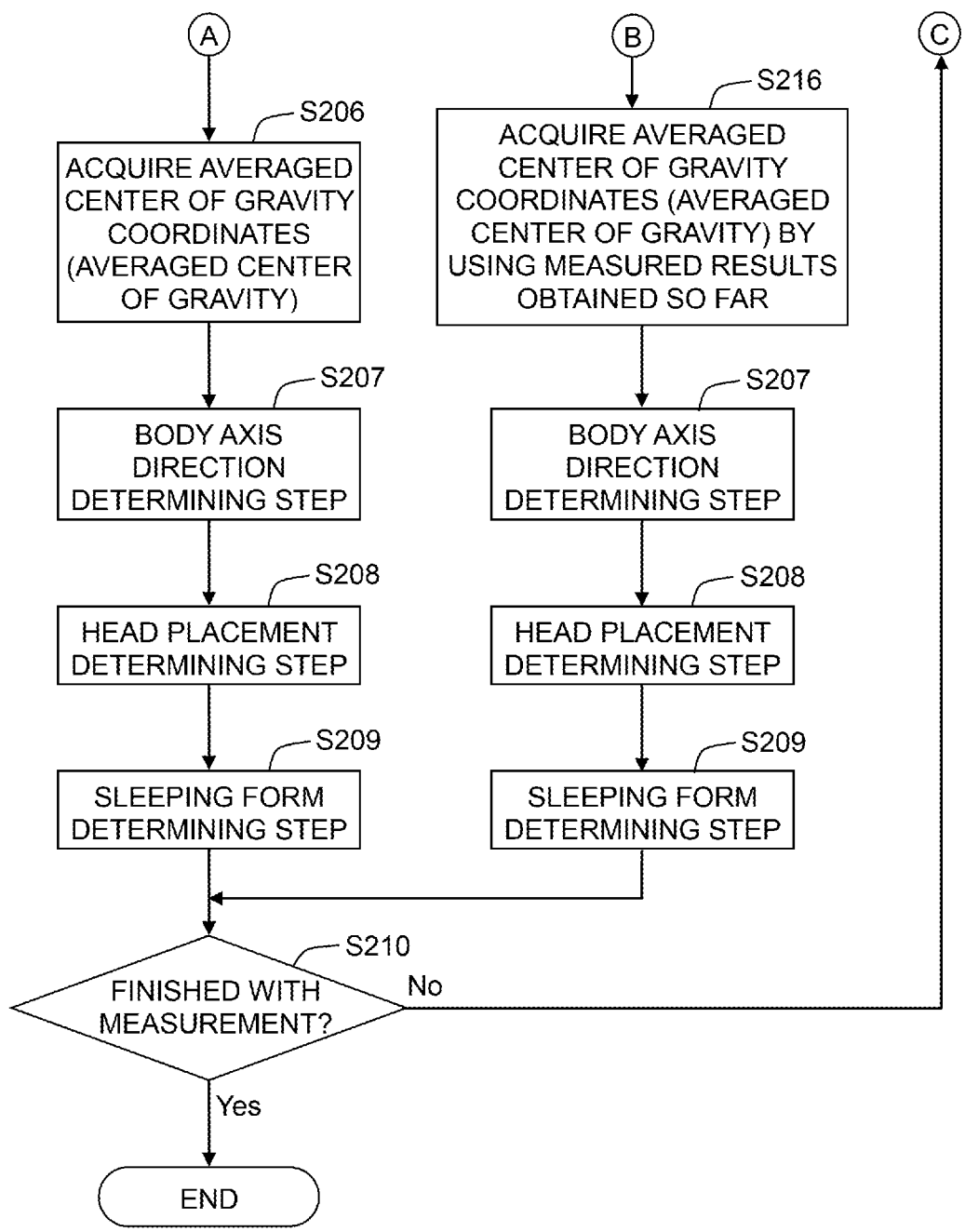

FIGS. 14A and 14B is a flow chart depicting the method of the modified embodiment. In the same manner as the detecting method of the embodiment, the detecting method of this modified embodiment also includes a step of calculating the center of gravity position, a step of determining the body axis direction, a step of determining the head placement, and a step of determining (judging) the sleeping form. However, in each of those steps, a different process from that of the embodiment will be performed. Hereinbelow, each of the steps will be explained with reference to the flow chart of FIGS. 14A and 14B as appropriate.

<Center of Gravity Position Calculating Step>

The center of gravity position calculating step of the modified embodiment (S201 to S206, and S216) is different from the center of gravity position calculating step (S102) of the above embodiment in that the calculating step of the modified embodiment also acquiring an average value of the position G (X, Y) for each predetermined detection period T1, T2, . . . , and TN, in addition to the position G (X, Y) of the center of gravity G at each time t.

Figure 15:
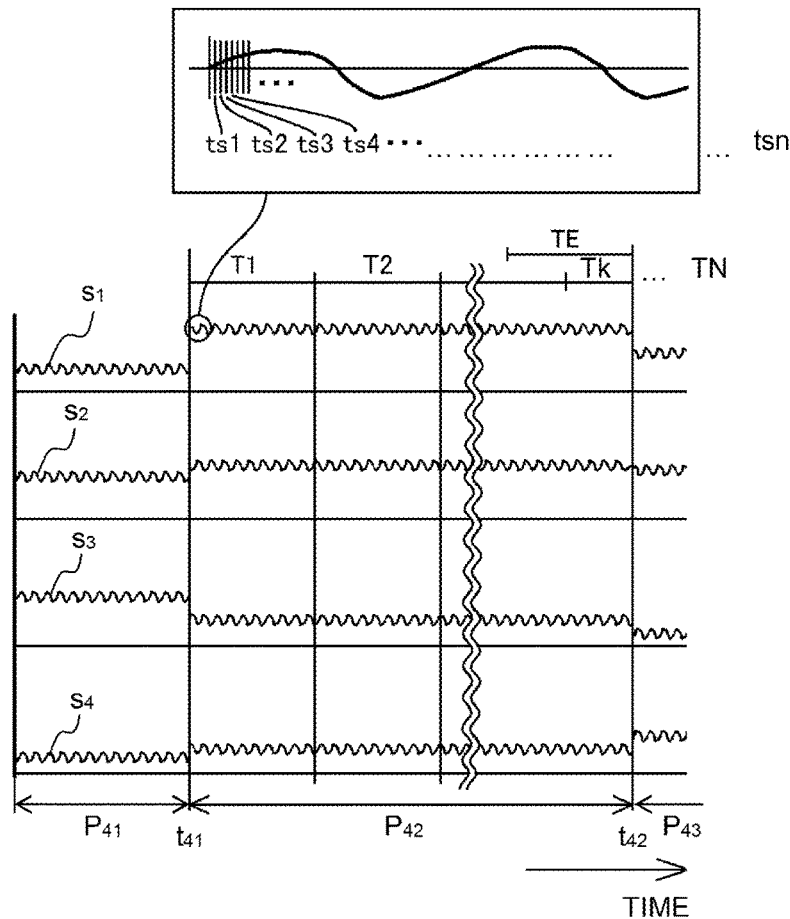
FIG. 15 is an illustrative view depicting how periodic detection of load values during a detection period T1 is performed.

FIG. 15 depicts one example of the load signals $s_1$ to $s_4$ fed from the load detectors 11 to 14 during the periods $P_{41}$, $P_{42}$, and $P_{43}$ each corresponding to a period from one change in posture to the next change in posture. In FIG. 15, a minute waveform depicted on each signal conceptually indicates that the respiration waveform BW is included in each of load signals $s_1$ to $s_4$. Note that, in the explanation of the embodiment described above, the situation in which the subject moves at the times $t_{11}$, $t_{12}$, and $t_{13}$ was explained with reference to FIG. 5. A movement of the subject on the bed such as described here or in the above embodiment is referred to in the present specification as a change in posture or a body motion.

Each of the periods $P_{41}$, $P_{42}$, and $P_{43}$ corresponds to a period during which the subject S is static in an almost constant posture. Therefore, the load signals $s_1$ to $s_4$ show an almost constant value throughout each period. On the other hand, the subject S changes his/her posture at the times $t_{41}$ and $t_{42}$. Hence, the load signals $s_1$ to $s_4$ vary at the time $t_{41}$ and the time $t_{42}$.

One example of the method for acquiring a position G0 (X0, Y0) of an averaged center of gravity G0 for each of the predetermined detection periods T1, T2, . . . , and TN, is as follows.

In FIG. 15, the detection period T1 is included in the period $P_{42}$ during which the subject S is static in the almost constant posture. Therefore, during the detection period T1, the subject S is in the constant posture. In this case, the center of gravity position calculating unit 31 detects the load value of each of the load signals $s_1$ to $s_4$ at the times ts1, ts2, . . . , and tsn in the detection period T1. The upper right enclosure in FIG. 15 depicts, in an enlarged manner, a total of n performances of detecting of the load value based on the load signal $s_1$ at the times ts1, ts2, . . . , and tsn.

The center of gravity position calculating unit 31 uses a set of load values detected at every time in the above manner to calculate the position G1 (X1, Y1), G2 (X2, Y2), . . . , and Gn (Xn, Yn) of the center of gravity G at each time, by applying the aforementioned Formula 1 and Formula 2. The position G0 (X0, Y0) of the averaged center of gravity G0 during the detection period T1 is acquired as a simple average of the positions G1 (X1, Y1), G2 (X2, Y2), . . . , and Gn (Xn, Yn) of the center of gravity G at each time.

As another example, an explanation will be made on an exemplary case of a detection period Tk started right before the time $t_{42}$ of FIG. 15. In this case, too, the positions G1 (X1, Y1), G2 (X2, Y2), . . . of the center of gravity G at each time are calculated in the same manner as in the case of the detection period T1 described above. However, different from the case of the detection period T1, the time $t_{42}$ comes before performing a sufficient number of calculations for acquiring the position G0 (X0, Y0) of the averaged center of gravity G0, such that the subject S will change in posture (there is change in the values of the load signals $s_1$ to $s_4$).

Thus, in this case, by resetting the interval between the time $t_{42}$ when the subject S changes in posture and the time earlier than the time $t_{42}$ by a predetermined period of time, as a detection period TE (having the same length as the detection periods T1 and T2), the position G0 (X0, Y0) of the averaged center of gravity G0 during the detection period TE described above is calculated by the same method as to calculate the position G0 (X0, Y0) of the averaged center of gravity G0 during the detection period T1.

The flow chart of FIGS. 14A and 14B depicts the steps S201 to S206 and S216 for acquiring the averaged center of gravity G0 during the detection periods T1, T2, . . . , and TN.

First, in the step S201, the center of gravity position calculating unit 31 sets k=0 for the number of times k the load values of the load signals $s_1$ to $s_4$ are detected. Next, in the step S202, the center of gravity position calculating unit 31 determines whether or not the subject S exhibits a body motion (change in posture). In particular, the center of gravity position calculating unit 31 determines whether or not any of the load signals $s_1$ to $s_4$ has changed beyond a predetermined range.

If there is no change beyond the predetermined range in the load signals $s_1$ to $s_4$ ("no" in the step S202), then the center of gravity position calculating unit 31 sets k=k+1 for the number of times k of detections (step S203). Then, the center of gravity position calculating unit 31 acquires the load values of the load signals $s_1$ to $s_4$, calculates the position of center of gravity Gk+1, and lets the storage unit 4, for example, store the calculated position of center of gravity Gk+1 (step S204). Then, in the step S205, the center of gravity position calculating unit 31 determines whether or not the number of times k of detections is less than n and, if it is less than n, then the process returns to the step S202. Thereafter, the step S202 to the step S205 are repeated until either the number of times k of detections reaches n or the subject S exhibits the body motion.

In the step S205, if the center of gravity position calculating unit 31 determines that the number of times k of detections is n, the center of gravity position calculating unit 31 lets the process move to the step S206. Then, the center of gravity position calculating unit 31 acquires the position G0 (X0, Y0) of the averaged center of gravity G0 by using the n pieces of positions of center of gravity G1, G2, . . . , and Gn stored at that time (step S206).

Further, in the step S202, if it is determined that the subject S has exhibited the body motion, the center of gravity position calculating unit 31 lets the process move to the step S216. In the step S216, as described earlier on, the interval between the time at which the subject S changes in posture and the time earlier than that time by the predetermined period of time is newly set as the detection period TE, and then, the position G0 (X0, Y0) of the averaged center of gravity G0 during the detection period TE is acquired.

<Body Axis Direction Determining Step>

In the body axis direction determining step of the modified embodiment (S207), which is different from the body axis direction determining step of the embodiment described above (S103), the body axis direction determining unit 32 uses the position G0 (X0, Y0) of the averaged center of gravity G0 calculated in the above step, to calculate the extending direction of the body axis SA of the subject S.

The body axis direction determining unit 32 calculates the extending direction of the body axis SA by, for example, the following method.

In one exemplary method, an averaged inclination angle "a" that is an average of angles between X axis and segments each linking the averaged center of gravity G0 (X0, Y0) and each of n pieces of the center of gravity positions G1 (X1, Y1), . . . , Gk1 (Xk1, Yk1), . . . , Gk2 (Xk2, Yk2), . . . , and Gn (Xn, Yn) are acquired by the following Formula 3:

$$a = \frac{\sum_{k=1}^{n} \arctan\left(\frac{Yk}{Xk}\right)}{n}$$

Figure 16:
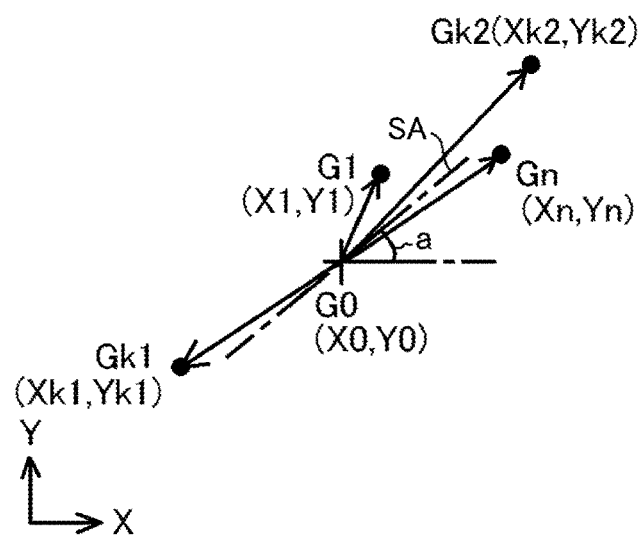
FIG. 16 is an illustrative view explaining an exemplary method for calculating a body axis direction.

In this method, a segment which extends through the averaged center of gravity G0 (X0, Y0), and which inclines with respect to X axis by the averaged inclination angle "a" is regarded as indicating the position of the body axis SA. FIG. 16 depicts the body axis SA acquired in this manner.

Figure 17:
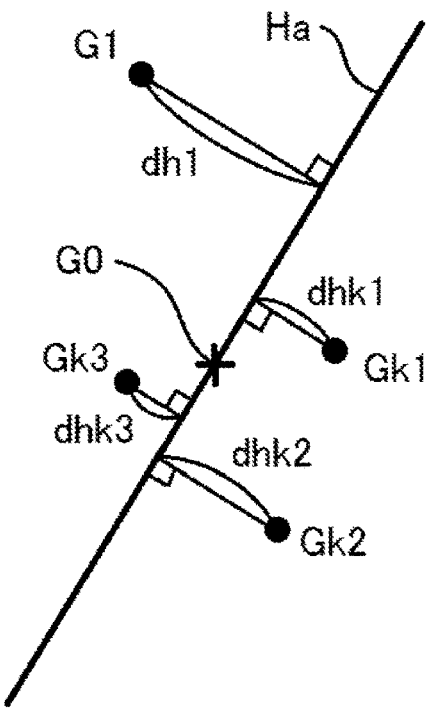
FIG. 17 is an illustrative view explaining another exemplary method for calculating the body axis direction.

In another exemplary method, a line Ha described below will be considered as indicating the position of the body axis SA. The line Ha is a line that passes through the average center of gravity G0 and that minimize a standard deviation of straight-line distances dh1, ..., dhk1, ..., dhk2, ..., dhk3, ..., dhn which are straight-line distances between the line and the centers of gravity G1, ..., Gk1, ..., Gk2, ..., Gk3, ..., Gn, respectively. An example of the line Ha is depicted in FIG. 17.

<Head Placement Determining Step>

In the head placement determining step (S208) of the modified embodiment, which is different from the head placement determining step (S104) of the embodiment described above, the head placement determining unit 33 determines the head placement of the subject S on the basis of the center of gravity positions G1 (X1, Y1), ..., Gk1 (Xk1, Yk1), ..., Gk2 (Xk2, Yk2), ..., and Gn (Xn, Yn) calculated in the above step, and the averaged center of gravity G0 (X0, Y0).

In the head placement determining step S208 of the modified embodiment, the method for determining the head placement is as follows.

Figure 18:
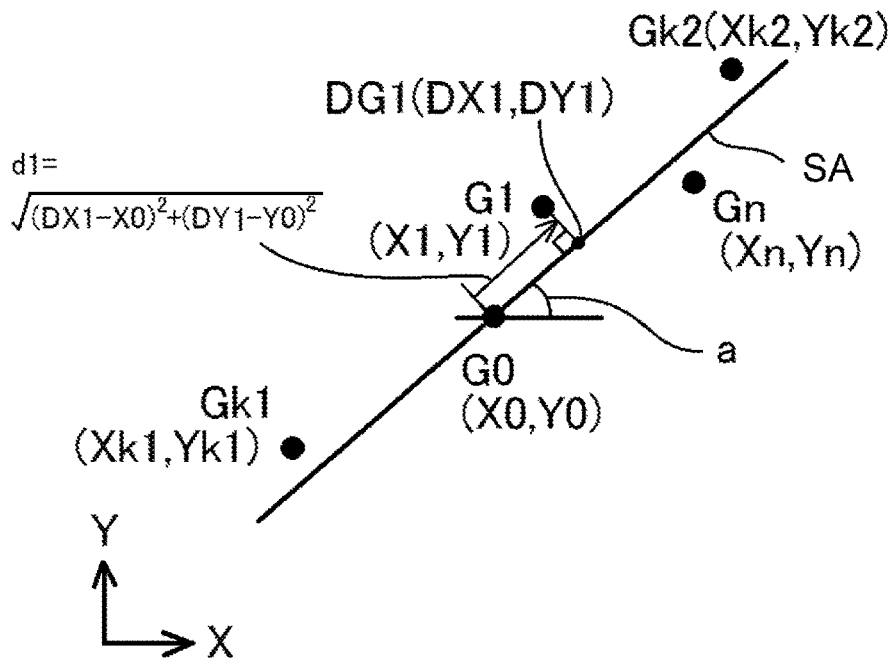
FIG. 18 is an illustrative view explaining a method for acquiring a waveform based on a movement of a center of gravity position.

First, the head placement determining unit 33 calculates the temporal variation of the center of gravity G as a waveform. In particular, the head placement determining unit 33 first acquires the coordinate DG1 (DX1, DY1) of the feet on the vertical line to the body axis SA from the center of gravity G1 just as depicted in FIG. 18, and then acquires a distance d1 between that feet position and the position G0 (X0, Y0) of the averaged center of gravity G0, by the following Formula 4:

$$d1 = \sqrt{(DX1-X0)^2 + (DY1-Y0)^2}$$

Figure 19A:
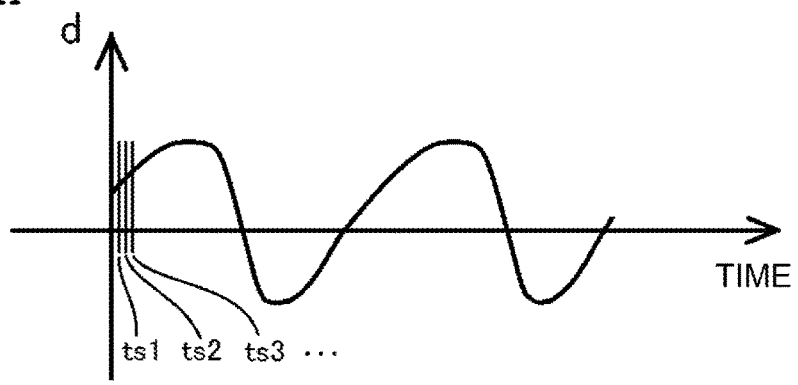
FIG. 19A depicts an exemplary waveform based on the movement of the center of gravity position.

Next, the head placement determining unit 33 performs the same calculation as described above also for the centers of gravity G2, ..., and Gn to acquire distances d2, ..., and dn. If the values of distance d acquired in this manner are laid out on a graph with the distance d as the vertical axis and the time axis as the horizontal axis, then a graph such as depicted in FIG. 19A will be obtained. That is, FIG. 19A plots, from left to right along the time axis, the distance d1 calculated from the center of gravity G1, the distance d2 calculated from the center of gravity G2, ..., the distance dk1 calculated from the center of gravity Gk1, ..., the distance dk2 calculated from the center of gravity Gk2, ..., and the distance dn calculated from the center of gravity Gn. As understood from FIG. 18, FIG. 19A corresponds to the waveform depicting an image of the temporal variation of the center of gravity G along the direction of the body axis SA with the averaged center of gravity G0 as the center. Note that in FIG. 19A, the distance d extending along the positive X axis from the averaged center of gravity G0 in FIG. 18 has a positive value, whereas the distance d extending along the negative X axis from the averaged center of gravity G0 has a negative value.

Figure 19B:
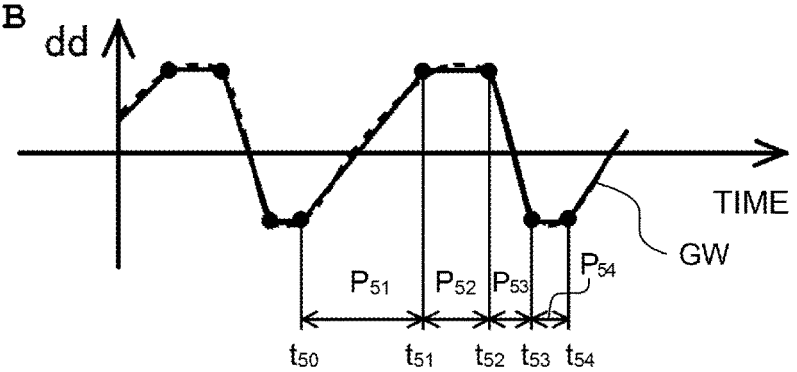
FIG. 19B is a waveform obtained by simplifying the waveform of FIG. 19A.

FIG. 19B schematically depicts the waveform GW of FIG. 19A. In FIG. 19B, the subject S starts an inhalation at a time $t_{50}$. The subject S ends the inhalation at a time $t_{51}$. The subject S starts the expiration at a time $t_{52}$. The subject S ends the expiration at a time $t_{53}$. The subject S starts the next inhalation at a time $t_{54}$.

The inventors of the present invention have observed the waveform GW of FIGS. 19A and 19B under various conditions, and found out that there is such a common feature as below.

That is, in the waveform GW, too, in the same manner as in the head-side waveform HW and the feet-side waveform LW described earlier on, the inhalation period $P_{51}$ during which the subject S is in inhalation is longer than the expiration period $P_{53}$ during which the subject S is in expiration.

Further, in the waveform GW, too, in the same manner as in the head-side waveform HW and the feet-side waveform LW described earlier on, an almost flat part appears in the vicinity of the peak of the waveform during the post-inhalation hold period $P_{52}$ from the time $t_{51}$ when the subject S ends the inhalation to the time $t_{52}$ when the subject S starts the expiration, and during the post-expiration hold period $P_{54}$ from the time $t_{53}$ when the subject S ends the expiration to the time $t_{54}$ when the subject S starts the inhalation. Then, the post-inhalation hold period $P_{52}$ is longer than the post-expiration hold period $P_{54}$.

Further, when the subject S exhibits the head-side waveform HWm or the feet-side waveform LWm, the waveform GW also has the same feature as the head-side waveform HWm or the feet-side waveform LWm.

The waveform GW has the above features, and the chevron waveform or the notch waveform representing the inhalation period $P_{51}$, the post-inhalation hold period $P_{52}$ and the expiration period $P_{53}$ is an asymmetrical waveform along the time axis with respect to the center of the post-inhalation hold period $P_{52}$ (between the front and the rear of the center). This is because the waveform GW is also a fluctuation based on the center of gravity movement of the subject S caused by the respiration, in the same manner as the head-side waveforms HW and HWm, and the feet-side waveforms LW and LWm. Therefore, the head placement determining unit 33 can analyze the waveform GW so as to determine the head placement of the subject S based on at least one of the inhalation period Psi, the post-inhalation hold period $P_{52}$, the expiration period $P_{53}$, and the post-expiration hold period $P_{54}$.

In particular, for example, the head placement determining unit 33 can analyze the waveform GW depicted in FIG. 19B, so as to acquire that the post-inhalation hold period $P_{52}$ appears on the positive side. The post-inhalation hold period $P_{52}$ appearing on the positive side means the center of gravity G has been moved to the positive side after inhalation. Therefore, the head placement determining unit 33 can determine that the feet of the subject S is placed on the positive side on the X axis in FIG. 18 to which the center of gravity moves during the inhalation, while the head of the subject S is placed on the negative side, i.e., the opposite side.

<Sleeping Form Determining Step>

The sleeping form determining step (S209) of the modified embodiment is different from the sleeping form determining step (S105) of the embodiment described above, in that the sleeping form determining unit 34 determines the sleeping form of the subject S on the basis of the waveform GW calculated in the foregoing step.

According to the findings of the inventors, if the subject S changes in sleeping form between the supine position, the recumbent position, and the prone position, then the waveform GW shows the same change in the waveform as the head-side waveforms HW and HWm depicted in FIGS. 11A to 12C. Therefore, the sleeping form determining unit 34 analyzes the waveform GW, for example, and acquires the length of the inhalation period $P_{51}$. Then, it is possible for the sleeping form determining unit 34 to determine that if the length of the inhalation period $P_{51}$ is smaller than a predetermined value, then the subject S is in the supine position, if the length of the inhalation period $P_{51}$ is almost the same as the predetermined value, then the subject S is in the recumbent position, and if the length of the inhalation period $P_{51}$ is larger than the predetermined value, then the subject S is in the prone position.

The process of the modified embodiment finally determines whether or not the measurement is finished at the step S210 (FIGS. 14A and 14B). If the measurement is not finished, then the process returns to the step S201.

In the modified embodiment, the extending direction of the body axis, the head placement, and the sleeping form of the subject are determined based on the temporal change of the center of gravity position. Here, the center of gravity position is calculated on the basis of the load detected by a plurality of load detectors. Therefore, determining the extending direction of the body axis, the head placement and the sleeping form of the subject on the basis of the temporal change of the center of gravity position is also included in determining the extending direction of the body axis, the head placement and the sleeping form of the subject on the basis of the variation of the load detected by the load detectors.

Note that, in the above embodiment, the head placement determining unit 33 identifies the position, in the waveform, corresponding to the inhalation period $P_{31}$, based on such a relationship that the inhalation period $P_{31}$ is longer (or shorter) than the expiration period $P_{33}$. However, the method for identifying the position of the inhalation period $P_{31}$ is not limited to that. According to a research of the inventors of the present invention, it is known that when the subject S is snoring, the respiration waveform BW minutely oscillates with a period far shorter than the respiratory period (about 3 to 5 seconds) in the inhalation period $P_{31}$. Therefore, if the position, in the respiration waveform BW, at which the minute oscillation with the short period (high frequency) occurs due to the snoring has been identified based on an analysis of the respiration wave form BW, then based on that, it is possible to identify the position of the inhalation period $P_{31}$.

Further, in the embodiment described above, the head placement determining unit 33 determines whether the respiration waveform BW is the head-side waveform HW or the feet-side waveform LW by identifying the position, of the respiration waveform BW, corresponding to the inhalation period $P_{31}$. However, without being limited to that, for example, as described above, both the head-side waveform HW and the feet-side waveform LW have such a feature that the post-inhalation hold period $P_{32}$ is longer than the post-expiration hold period $P_{34}$, but they differ from each other in that those periods appear whether in the chevron side (peak side) or in the notch side (trough side). Likewise, both the head-side waveform HWm and the feet-side waveform LWm have such a feature that the post-inhalation hold period $P_{32}$ is shorter than the post-expiration hold period $P_{34}$, but they differ from each other in that those periods appear whether in the chevron side or in the notch side. Therefore, the head placement determining unit 33 may determine whether the respiration waveform BW is the head-side waveforms HW, HWm or the feet-side waveforms LW, LWm by distinguishing the post-inhalation hold period $P_{32}$ and the post-expiration hold period $P_{34}$ on the basis of how long the period is, and then identifying whether they appear in the chevron side or in the notch side.

Further, as another example, the storage unit 4 may store referential waveforms corresponding to the head-side waveform HW, HWm and the feet-side waveform LW, LWm while the head placement determining unit 33 may determine whether the respiration waveform BW is the head-side waveform HW, HWm or the feet-side waveform LW, LWm on the basis of a comparison between the respiration waveform BW and the referential waveform stored in the storage unit 4, without analyzing the shape of the respiration waveform BW.

In the embodiment described above, the sleeping form determining unit 34 analyzes the respiration waveform BW and compares the length of the inhalation period $P_{31}$ with the predetermined value, so as to determine the sleeping form of the subject S. However, the method for the sleeping form determining unit 34 to determine the sleeping form of the subject S is not limited to that but, for example, the storage unit 4 may store referential waveforms corresponding to the supine position, the recumbent position, and the prone position while the sleeping form determining unit 34 may determine the sleeping form of the subject S on the basis of a comparison between the respiration waveform BW and the referential waveforms stored in the storage unit 4.

In the embodiment described above, the head placement determining unit 33 determines the head placement of the subject S after the body axis direction determining unit 32 determines the extending direction of the body axis SA of the subject S. However, without being limited to that, the head placement determining unit 33 can determine the head placement of the subject S without determining the extending direction of the body axis SA of the subject S.

In particular, the head placement determining unit 33 analyzes the load signals $s_1$ to $s_4$ fed from the load detecting unit 1 and determines whether the respiration waveform BW included in each of the load signals $s_1$ to $s_4$ is the head-side waveform HW, HWm or the feet-side waveform LW, LWm. Then, the head placement determining unit 33 determines that the subject S places his/her head in an area corresponding to the load detectors sending the respiration waveform BW determined as the head-side waveform HW, HWm, whereas the subject S places his/her feet in an area corresponding to the load detectors sending the respiration waveform BW determined as the feet-side waveform LW, LWm.

In the embodiment described above, the sleeping form determining unit 34 determines the sleeping form of the subject S after the head placement of the subject S has been determined. However, without being limited to that, the sleeping form determining unit 34 may determine the sleeping form of the subject S without determining the extending direction of the body axis SA of the subject S and/or the head placement of the subject S. As described earlier on, the difference in sleeping form presents a feature difference in the load waveform. Thus, there are cases where it is possible to determine the sleeping form of the subject S only based on the load signals. In such cases, the respiration waveform BW may be taken out from the load signals by the sleeping form determining unit 34 rather than by the head placement determining unit 33.

The body state detecting apparatus 100 of the above embodiment includes all of the body axis direction determining unit 32, the head placement determining unit 33 and the sleeping form determining unit 34. However, the body state detecting apparatus 100 may be configured to include any one or two thereof only. Each of the body axis direction determining unit 32, the head placement determining unit 33 and the sleeping form determining unit 34 is a specific example of the body state detecting unit of the present disclosure.

The center of gravity position calculating unit 31 of the body state detecting apparatus 100 of the embodiment described above may use the calculated center of gravity G position at each time t to acquire the locus of the moving center of gravity G (the center of gravity locus). The storage unit 4 may store the acquired center of gravity locus.

A respiratory rate calculation unit (not depicted) for acquiring the respiratory rate of the subject S may be constructed in the control unit 3 of the body state detecting apparatus 100 of the embodiment described above. The respiratory rate calculation unit can acquire the respiratory rate of the subject S, for example, by extracting the locus of the moving center of gravity caused by the respiration from the center of gravity locus acquired by the center of gravity position calculating unit 31, and then, analyzing the oscillation frequency of the extracted locus. The locus of the moving center of gravity caused by the respiration can be extracted by, as one example, identifying the center of gravity locus oscillating periodically in a specific direction as the center of gravity locus caused by the respiration, and extracting such a center of gravity locus.

The locus of the moving center of gravity caused by the respiration can be extracted, as one example, by the following method.

Figure 20A:
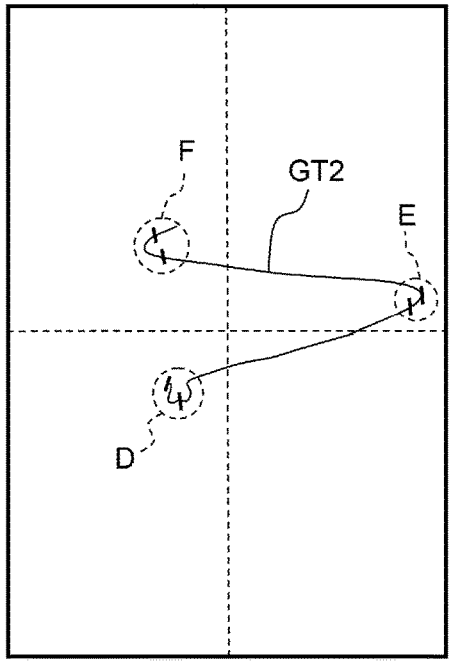
FIG. 20A depicts an exemplary center of gravity locus of the subject.

First, a body motion information determining unit (not depicted) constructed in the control unit 3 is used to take out, for example, a center of gravity locus GT2 of the subject S through one minute from the storage unit 4. FIG. 20A depicts one example of the center of gravity locus GT2 taken out. The center of gravity locus GT2 depicted in FIG. 20A presents one reciprocating large body motion (such as a turn-over motion or the like) of the subject S on the bed along the left/right direction. Further, FIG. 20A depicts images of movement of the center of gravity G of the subject S in areas D, E and F each observed during a stable body posture period in which no large body motion is performed. The movements of the center of gravity G in the areas D, E, and F occur due to some small body motion, respiration and the like of the subject S. Note that, in the present disclosure, the term "large body motion" principally includes the turning over and other discrete body motion accompanied by the movement of the body portion (trunk), and the large body motion also arises, for example, when the subject is painful or the subject awakens. When the term is defined in view of the movement of the center of gravity, the term means the body motion in which the center of gravity G is moved beyond a predetermined distance d in a certain direction within a certain period. Therefore, it is arbitrary that what one of the body motions of the subject S is regarded as the "large body motion". It is possible to determine what one is regarded as the "large body motion" on the basis of the value of the predetermined distance d. It is also possible to define that the large body motion is the movement of the center of gravity which is larger than the movement of the center of gravity caused by the respiration to such an extent that the relative distinction can be made (for example, the former is not less than several times of the latter).

A large body motion determining unit (not depicted) included in the body motion determining unit (not depicted) determines the locus of the center of gravity movement caused by the large body motion of the subject S, and extracts the same from the center of gravity locus GT2 (a large body motion determining step). If the center of gravity G moves in a certain direction beyond a certain distance within a certain time, e.g., moves to displace between areas within the certain time, then the respiratory rate calculating unit determines a large body motion occurs, and extracts the center of gravity locus GT2 during that period.

Figure 20B:
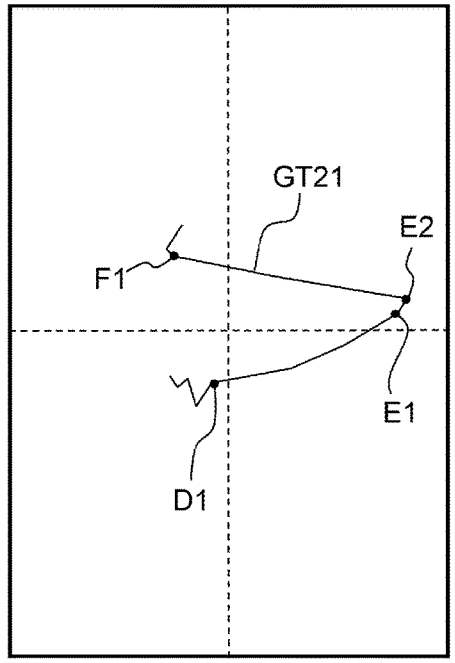
FIG. 20B depicts a center of gravity locus obtained by converting the center of gravity locus depicted in FIG. 20A into a low sampling frequency.

In the large body motion determining step, the following method is used to determine whether or not the center of gravity G moves in the certain direction beyond the certain distance within the certain time. First, the center of gravity locus GT2 depicted in FIG. 20A is converted into a center of gravity locus GT21 based on a lower sampling frequency (FIG. 20B). The conversion can be performed by thinning out the data of the center of gravity position G acquired at a sampling frequency of 0.1 seconds and/or by using a moving average process. Alternatively, the conversion can also be performed by subjecting the center of gravity locus GT2 to the frequency resolution and then extracting the predetermined low frequency component by means of a low-pass filter.

With reference to FIG. 20B, the locus between the point D1 and the point E1 exhibits, for example, the movement in the right direction within 0.5 seconds beyond 30 cm. Therefore, the respiratory rate calculating unit determines that the locus in this interval is the locus of the large body motion. The respiratory rate calculating unit removes the locus in this interval from the center of gravity locus GT2. Similarly, the locus between the point E2 and the point F1 exhibits, for example, the movement in the left direction within 0.5 seconds beyond 30 cm. Therefore, the large body motion information determining unit determines that the locus in this interval is the locus of the large body motion. The large body motion information determining unit removes the locus in this interval from the center of gravity locus GT2. Note that the movement from the point D1 to the point E1 and the movement from the point E2 to the point F1 may be identified as the movements related to the large body motion on the basis of the fact that each movement is a movement from one area to another area.

Figure 21A:
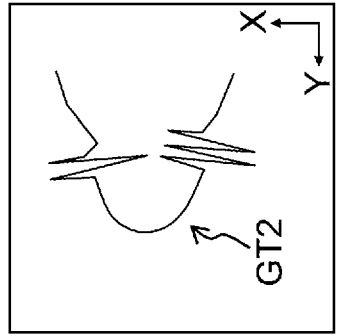
FIGS. 21A, 21B, and 21C depict loci resulted from removing the locus of the center of gravity movement caused by a large body motion of the subject, from the center of gravity locus of the subject on the bed as depicted in FIG. 20A.
Figure 21B:
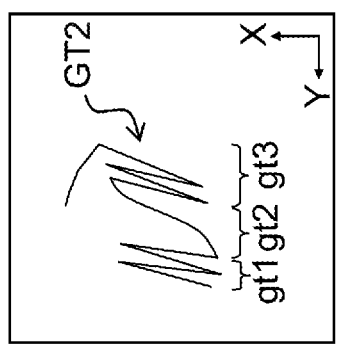
Figure 21C:
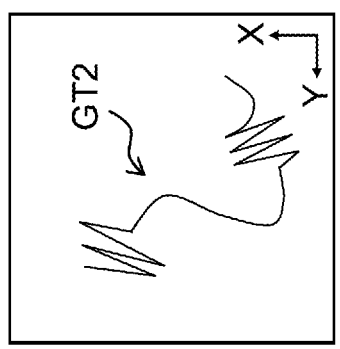

The loci, obtained by removing the locus of the large body motion from the center of gravity locus GT2 depicted in FIG. 20A, are depicted in FIGS. 21A to 21C. FIG. 21A depicts the center of gravity locus GT2 in the area D, FIG. 21B depicts the center of gravity locus GT2 in the area E, and FIG. 21C depicts the center of gravity locus GT2 in the area F. Each of the loci is the center of gravity locus GT2 during the stable posture period (the period when the large body motion does not occur).

Note that it is desirable that the low sampling frequency has the period which is short (the frequency which is large) to such an extent that the large body motion is sufficiently extracted, and the low sampling frequency has the period which is long (frequency which is small) to such an extent that no influence is exerted by the variation of the center of gravity caused by any other factor than the large body motion such as the small body motion, the respiration or the like. Further, the extent of the time and the extent of the distance, on the basis of which it is to be determined that the large body motion is caused when the movement occurs within that time by that distance, can be optimized in conformity with the feature of the apparatus of the body state detecting apparatus 100.

Subsequently, the small body motion information determining unit of the body motion information determining unit determines and extracts the locus of the center of gravity movement caused by the small body motion of the subject S from the center of gravity locus GT2 during the stable posture period (small body motion determining step). The step of removing the locus of the center of gravity movement caused by the small body motion of the subject S from the center of gravity locus GT2 during the stable posture period will be explained. Here, a procedure in which the small body motion locus and the respiration locus are separated from the center of gravity locus GT2 in the area E (FIG. 21B) will be explained as an example. Note that in the present disclosure, the term "small body motion" means such a movement that the entire body of the subject S does not greatly move but only parts of the body, i.e., hands, feet, and/or face (head) move. When the small body motion is defined in view of the movement of the center of gravity, it means the body motion in which the center of gravity G is moved within a range not exceeding the predetermined distance d in the direction different from the direction of the center of gravity movement caused by the respiration of the subject S. The small body motion can be also recognized as the small movement of the center of gravity to such an extent that the small body motion can be distinguished from the large body motion (for example, the former is not more than a fraction (one-severalth) of the latter).

In the small body motion determining step, the center of gravity locus, which is calculated by the respiratory rate calculating unit using data of past measurement, and which oscillates periodically in specified directions, is identified as the center of gravity locus based on the respiration. The center of gravity locus, which is different from the center of gravity locus as identified above, is identified as the center of gravity locus based on the small body motion.

With reference to FIG. 21B, the center of gravity locus GT2 includes the portions gt1 and gt3 which represent the movement of the center of gravity G caused by the respiration and the portion gt2 which represents the movement of the center of gravity G caused by the small body motion (note that the portion gt2 represents the movement of the center of gravity G caused by the respiration as well). The portion gt2, which represents the movement of the center of gravity G caused by the small body motion, does not periodically oscillate in any specified direction, unlike the center of gravity loci of the portions gt1 and gt3 which represent the movement of the center of gravity G caused by the respiration.

Therefore, one method is available to separate and extract the locus of the center of gravity movement caused by the small body motion. That is, only the center of gravity locus (gt1, gt3), which oscillates periodically in specified directions, is extracted, and it is regarded as the respiratory component of the center of gravity movement. Then, the other portion (gt2) is separated and extracted as the small body motion. The separation and the extraction as described above, for example, can be carried out in accordance with the method as described below. The center of gravity variation, which is repeated periodically and which is included in the center of gravity variations provided during a past certain period in the stable respiration phase, is detected by means of the frequency analysis such as the Fourier analysis or the like. The direction of the center of gravity change exhibited in the corresponding frequency is detected, and this is regarded as the center of gravity variation caused by the respiration. After that, the difference between the presently measured center of gravity variation and the center of gravity variation caused by the respiration is extracted as the variation caused by the small body motion. In this procedure, if the component having the corresponding frequency is not included in the presently measured center of gravity variation and/or the amplitude of the presently measured center of gravity variation has largely changed, then it is regarded that the respiration condition of the subject S has changed, and obtaining the difference by using the center of gravity variation caused by the respiration is not performed.

Figure 22:
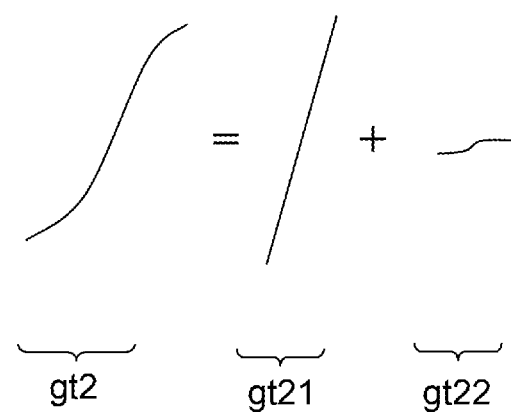
FIG. 22 is an illustrative view depicting an image of decomposing the center of gravity locus into a respiratory component and a small body motion component.
Figure 23:
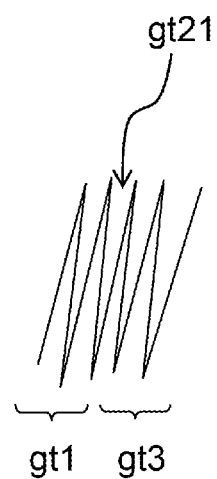
FIG. 23 depicts a respiratory component extracted from the center of gravity locus depicted in FIG. 21B.

Another method is available as depicted in FIG. 22. That is, the portion (gt2), which does not form the center of gravity locus oscillating periodically in any specified direction, is decomposed into the portion gt21 which constitutes a part of the center of gravity locus oscillating periodically in a specified direction and the other portion gt22. Then, only the portion gt21, which constitutes the part of the center of gravity locus oscillating periodically in the specified direction, is returned to the position between the portion gt1 and the portion gt3 to acquire the center of gravity locus as depicted in FIG. 23. This is used as the respiratory component of the center of gravity movement. Meanwhile, the portion gt22, which is decomposed from the portion gt2, is separated and extracted as the small body motion. The separation and the extraction as described above can be carried out in accordance with the foregoing method.

After that, the respiratory component of the center of gravity movement extracted by the body motion information determining unit is fed to the respiratory rate calculating unit. In the respiratory rate calculating unit, the respiratory rate is calculated by the same or equivalent means as that used in the embodiment described above. Note that it is also appropriate that the body motion information determining unit only determines the locus of the center of gravity movement caused by the large body motion and the locus of the center of gravity movement caused by the small body motion. That is, it is not necessarily indispensable to separate and extract the loci caused by the large and small body motions from the center of gravity locus. In this case, for example, the respiratory rate calculating unit extracts the respiratory component from the center of gravity locus with reference to the locus of the center of gravity movement caused by the large body motion and the locus of the center of gravity movement caused by the small body motion each of which was determined by the body motion information determining unit.

The respiratory rate calculating unit can further acquire the respiratory rate of the subject S per unit time, based on the oscillation frequency of the respiration waveform BW (FIGS. 10A and 10B) extracted from the load signals $s_1$ to $s_4$ fed from the load detectors 11 to 14, and/or the waveform GW (FIGS. 19A and 19B) calculated on the basis of the center of gravity G movement. Because those waveforms occur due to the respiration of the subject S, it is possible to acquire the respiratory rate of the subject S by analyzing those waveforms.

The waveforms are analyzed as follows, for example.

The total number of times of the reciprocating motion of the respiratory component extracted from the center of gravity locus GT2 depicted in FIGS. 21A to 21C represents the respiratory rate of the subject S per minute. Therefore, the respiratory rate calculating unit calculates the respiratory rate per minute of the subject S on the basis of the reciprocating motion of the respiratory component.

Specifically, the respiratory rate calculating unit firstly rotates the respiratory component of the center of gravity locus GT2 of the subject S so that the oscillating direction is coincident with the X axis direction. Subsequently, the respiratory rate calculating unit performs the filtering of a plurality of stages for the rotated respiratory component by using a multi-stage filter bank. The high frequency component is removed as the noise in the filtering at each stage. On the other hand, the filtering at the next stage is performed for the low frequency component obtained by the filtering at each stage. After performing the filtering a number of times corresponding to the predetermined number of stages, the low frequency component obtained at the final stage can be regarded as the number of times of respiration. Further, it is possible to perform the correct monitoring for whether the subject presents (exists) on the bed or does not present (exist) on the bed, by using the output from the load detecting unit 1 described above and the data of the respiratory rate calculating unit. For example, even when any baggage or the like is placed on the bed, the output of the load detecting unit 1 changes. However, if the respiratory rate is calculated by the respiratory rate calculating unit on the basis of the output of the load detecting unit 1, it is possible to determine that what exists on the bed is a human subject not the baggage or the like.

It is also possible to use other methods. Specifically, for example, the point positioned on the most positive side in the X axis direction and the point positioned on the most negative side in the X axis direction are firstly acquired from the respiratory component of the center of gravity locus GT2 oscillating in the X axis direction, and then, the intermediate value Xm of the X coordinates of the both points is calculated. The intermediate value Xm can be regarded as the center of oscillation of the center of gravity locus GT2 caused by the respiration of the subject S. Subsequently, the respiratory rate calculating unit acquires the number of times of movement of the center of gravity locus GT2 from the negative side to the positive side or from the positive side to the negative side in the X axis direction while crossing over the intermediate value Xm. Based on the acquired number of times, the respiratory rate calculating unit calculates the number of oscillations of the center of gravity locus GT2 caused by the respiration of the subject S, i.e., the respiratory rate.

A respiratory ventilation volume calculating unit (not depicted) for calculating respiratory ventilation volume (tidal volume) of the subject S may be constructed in the control unit 3 of the body state detecting apparatus 100 of the embodiment described above. The respiratory ventilation volume calculating unit estimates the ventilation volume of one respiration cycle of the subject S, on the basis of the locus of the center of gravity movement based on the respiration extracted by the respiratory rate calculating unit. Note that the respiratory ventilation volume is the physical amount corresponding to the depth of respiration.

The amplitude of one cycle of the locus of the center of gravity movement caused by the respiration corresponds to one respiration cycle. In the case of the large and deep respiration, when the lungs expand during the inhalation, then the diaphragm is greatly moved and lowered downwardly as compared with the ordinary inhalation, and the internal organs are also greatly moved downwardly. On the other hand, upon the expiration, i.e., when the lungs shrink, then the diaphragm is greatly moved and raised upwardly as compared with the ordinary expiration, and the internal organs are also greatly moved upwardly. On the contrary, in the case of the small and shallow respiration, the movement of the internal organs is small as compared with the ordinary state. According to the research performed by the inventors of the present invention, it has been found out that the slight movement of the center of gravity G caused by the movement of internal organs is affected by the size or magnitude of the respiration. Specifically, the amplitude is increased as compared with the ordinary state when the respiration is large and deep, while the amplitude is decreased as compared with the ordinary state when the respiration is small and shallow. The ventilation volume of one respiration cycle can be estimated by being correlated with the amplitude. For example, the following procedure is performed in advance. That is, the subject performs the large and deep respiration in a state in which the subject lies on his/her back on the bed, and the ventilation volume and the amplitude obtained in this state are recorded beforehand. Further, the subject performs the small and shallow respiration, and the ventilation volume and the amplitude obtained in this state are recorded beforehand. The respiratory ventilation volume is calculated using the amplitude of the acquired center of gravity locus based on the respiration. It is also possible to estimate a minute volume (a ventilation volume per minute) by estimating the ventilation volume of one respiration cycle. When the number of times of respiration per minute and the minute volume are known, it is thereby possible to monitor whether the respiratory condition of the subject S is comprehensively in a good state or in a bad state.

A heart rate calculating unit (not depicted) for acquiring the heart rate of the subject may be constructed in the control unit 3 of the body state detecting apparatus 100 of the embodiment described above. It is possible for the heart rate calculating unit to acquire the heart rate from, for example, the center of gravity locus acquired by the center of gravity position calculating unit 31. Because the heart rate has a unique periodicity formed of a set of combination of a plurality of center of gravity variations, the heart rate calculating unit 34 can estimate the displacement of the center of gravity considered to be caused by the present heart beat on the basis of the past calculation result. Therefore, the locus caused by the heart beat can be extracted from the center of gravity locus on the basis of the estimated displacement of the center of gravity, and the heart rate can be determined on the basis of the extracted locus.

The heart rate calculating unit can also calculate the heart rate by taking out the signal components of the frequency range of 0.5 Hz to 2.5 Hz corresponding to the heartbeat components, from the load signals $s_1$ to $s_4$ (FIG. 5) from the load detectors 11 to 14.

A physical condition determining unit (not depicted) for determining the sleep/wakefulness of the subject S may be constructed in the control unit 3 of the body state detecting apparatus 100 of the embodiment described above. As one example, the physical condition determining unit can determine the sleep/wakefulness of the subject S on the basis of the values of the respiratory ventilation volume and the respiratory rate of the subject S.

The physical condition determining unit may determine the physical condition of the subject by integrally using the data of various types of living body information (biological information) (for example, body weight, body motion, respiration, heartbeat, and the like). In this procedure, in order to raise the accuracy in determining the physical condition, it is also allowable to perform the machine learning based on the use of the teacher data.

That is, the function representing sleep state/a wakeful state is previously prepared by means of the fitting from a large number of pieces of living body information (labeled teacher data), and the data of various types of living body information, which is obtained from the body state detecting apparatus 100 of this embodiment, is substituted into the function so as to acquire the physical condition (i.e. the sleep or the wakefulness). That is, the algorithm of sleep/wakefulness can be obtained by the machine learning based on the use of various types of living body information such as the leaving from the bed, the settling on the bed, the large body motion, the small body motion, the respiration, the apnea, the snore, the utterance, and the heartbeat and the operation thereof (mathematical analysis including, for example, the four arithmetic operations, the integration, the differentiation, the frequency analysis, and the like), the various types of living body information being obtained from the body state detecting apparatus 100 with reference to the teacher data which is labeled as "during the wakefulness" or "during the sleep" and which is sampled from the subject.

The physical condition determining unit can also detect that the subject S settles on the bed BD and that the subject S leaves from the bed BD, on the basis of the change in the load values of the signals $s_1$ to $s_4$ fed from the load detectors 11 to 14. The determination of the settling of the subject S on the bed BD can be made, for example, depending on whether or not the increase in the total value of the load values indicated by the signals $s_1$ to $s_4$ fed from the load detectors 11 to 14 exceeds a predetermined value (the value is, for example, 40 kg, 55 kg, or 70 kg, and the value can be arbitrarily set by using, for example, the input unit 7). In the same manner, the determination of the leaving of the subject S from the bed BD can be made, for example, depending on whether or not the decrease in the total value of the load values indicated by the signals $s_1$ to $s_4$ fed from the load detectors 11 to 14 exceeds a predetermined value.

The physical condition determining unit can also detect that the subject S settles on the bed BD, and that the subject S leaves from the bed BD, on the basis of the center of gravity locus. The load from the bed BD is equally applied to the load sensors 11 to 14 during the period in which the subject S is absent on the bed. In other words, the center of gravity G is positioned at the center of the bed BD. Then, when the subject S is settled on the bed BD, the center of gravity G is greatly moved toward the position where the subject S is settled. The physical condition determining unit can detect the settlement of the subject S on the bed on the basis of the large movement of the center of gravity G as described above. The leaving of the subject S from the bed can also be detected in the same manner as described above.

The physical condition determining unit can also detect the fall of the subject S from the bed BD. Specifically, the physical condition determining unit can determine that the subject S has fallen from the bed BD if the subject S is in the sleep state but leaves from the bed. Further, the determination result may be displayed on the display unit 5. The determination result may be notified to the user of the body state detecting apparatus 100 by using the notifying unit 6. Note that the physical condition determining unit may determine that the subject S has left from the bed in accordance with his/her own intention if the subject S is in the wakeful state and leaves from the bed.

The physical condition determining unit may determine whether the subject S is alive or dead on the basis of various types of living body information acquired by the body state detecting apparatus 100. Specifically, for example, the physical condition determining unit can determine that the subject S is dead if all of the body motion (the movement of the center of gravity), the respiration, and the heartbeat of the subject S stop under a certain condition. The certain condition can be set on the basis of the judgment of a doctor or the like as the user.

The physical condition determining unit can also determine that the subject S is in the apnea condition which is a symptom of the sleep apnea syndrome. If a patient of the sleep apnea syndrome falls into the apnea during the sleep, then the respiration and the body motion stop during a certain period, and then the inhalation is performed greatly so as to cause the respiration and the body motion. On the other hand, the heartbeat continues throughout the above period. Therefore, the physical condition determining unit can detect that the apnea condition has occurred if the period, in which the respiration and the body motion stop but the heartbeat continues, continues for not less than a certain period of time.

The physical condition determining unit may display the determination result on the display unit 5. The determination result may be notified to the user of the body state detecting apparatus 100 by using the notifying unit 6 (nurse call). Further, the physical condition determining unit may label the living body information corresponding to the period during which the apnea condition occurred, when storing various types of measured living body information in the storage unit 4. With this, it is made easier to observe the symptom of the sleep apnea syndrome of the subject S after the event (ex post fact).

The physical condition determining unit of the body state detecting apparatus 100 of the embodiment described above can also detect the utterance and the snore of the subject S. In general, the utterance is performed simultaneously with the expiration. Therefore, for example, if any high frequency component is generated in the expiration period during the wakefulness or the sleep, it is possible to determine that the high frequency component is caused by the utterance. On the other hand, the snore generally occurs during the inhalation. Therefore, for example, if any high frequency component is generated in the inhalation period during the sleep, it is possible to determine that the high frequency component is caused by the snore.

When the center of gravity locus exhibits the movement which is different from the ordinary movement, then the notifying unit 6 of the body state detecting apparatus 100 of the embodiment described above may regard the movement as abnormal movement, and the notifying unit 6 may be used to perform the notification (nurse call). It is possible to appropriately set what kind of movement is the "movement different from the ordinary movement". As an example, if a predetermined body motion (a predetermined movement of the center of gravity) continues for not less than a certain period of time in a successive manner, then it is possible to determine that the "movement different from the ordinary movement" has occurred, and to perform the nurse call based on the determination. When the nurse call signal is received, it is also allowable to operate a camera which captures the situation of the bed.

It is also possible to measure the body weight of the subject S by using the center of gravity position calculating unit 31. The measurement of the body weight of the subject S can be realized by subtracting the weight of the bed BD previously stored in the storage unit 4 from the total value of the load values of the signals $s_1$ to $s_4$. Note that when the weight of the bed is not uniform among the four areas I to IV, the difference therebetween is stored beforehand as the bed weight corresponding to each of the load detectors. Further, it is desirable that the situation which provide any weight other than that of the subject S under the actual measurement, for example, the placement of any bedding, any baggage or the like is reflected to the weight of the bed.

In the embodiment described above, the body weight is measured by the center of gravity position calculating unit 31. However, it is also allowable to distinctly provide a body weight measuring unit in the control unit 3.

Note that in the embodiment described above, each of the load detectors 11, 12, 13, 14 is not limited to the load sensor having the beam-type load cell. It is also possible to use, for example, a force sensor.

Note that in the embodiment described above, the number of load detectors is not limited to four. It is also allowable to use five or more load detectors by providing an additional foot or additional feet for the bed BD. Alternatively, it is also allowable to arrange the load detectors for only three of the feet of the bed BD. Even when the three load detectors are used, it is possible to detect a position of the center of gravity G of the subject S on the plane of the bed BD provided that the three load detectors are not arranged on a straight line. Still alternatively, it is possible to detect the head placement and the sleeping form of the subject even with only two load detectors one of which is at the head side and the other at the feet side if the subject is restrained from body motion. Further, the detection of the sleep form of the subject may be performed based on single load detector.

Figure 24:
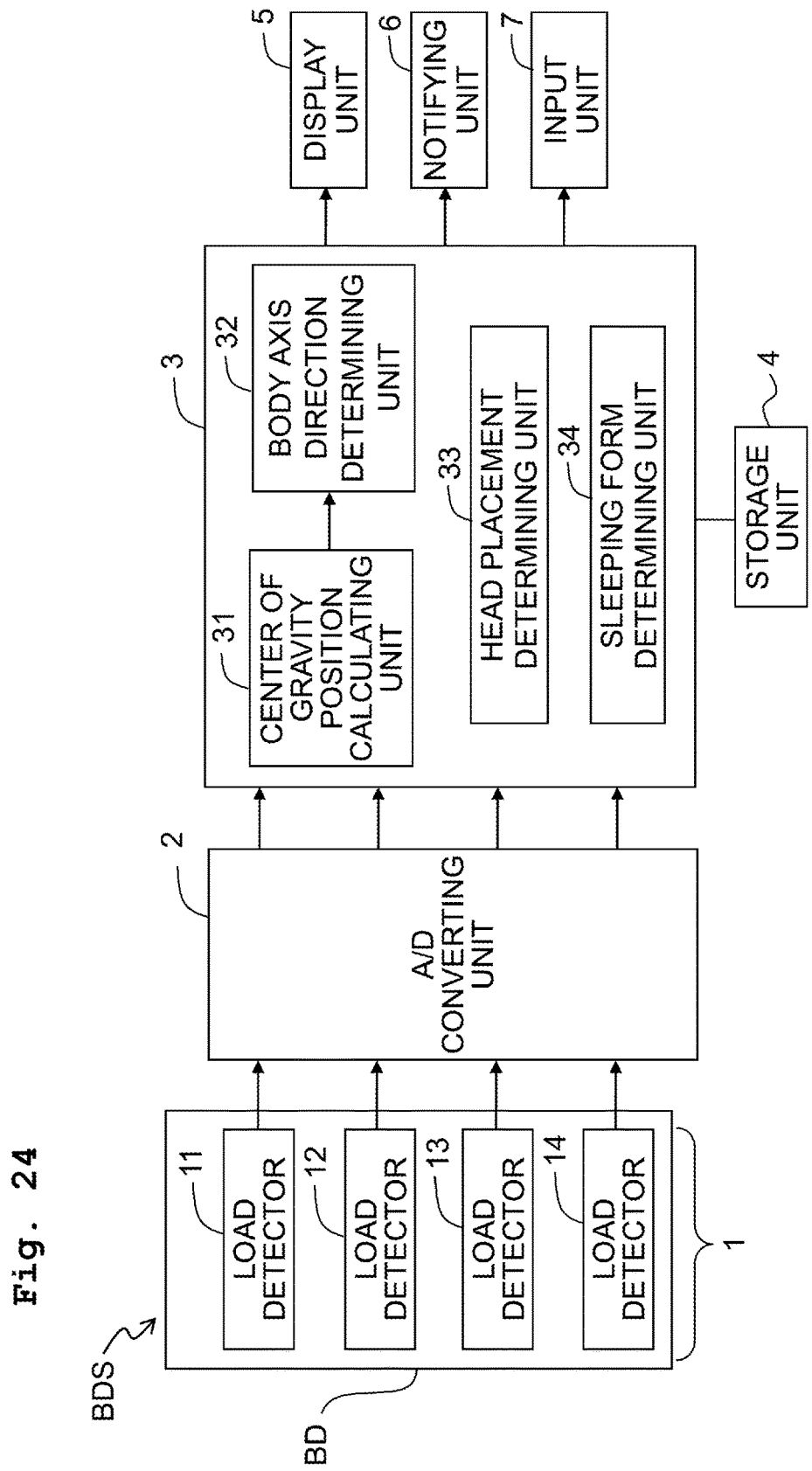
FIG. 24 is a block diagram depicting an overall configuration of a bed system according to the embodiment of the present disclosure.

Note that in the embodiment described above, the load detectors 11, 12, 13, 14 are arranged respectively under the casters $C_1$, $C_2$, $C_3$, $C_4$ attached to the lower ends of the feet of the bed BD. However, there is no limitation thereto. Each of the load detectors 11, 12, 13, 14 may be provided respectively between one of the four feet of the bed BD and the board of the bed BD. Alternatively, if each of the four feet of the bed BD can be divided into upper and lower portions, each of the load detectors 11, 12, 13, 14 may be provided between the upper foot portion and the lower foot portion. Further alternatively, the load detectors 11, 12, 13, 14 may be formed integrally with the bed BD to construct a bed system BDS comprising the bed BD and the body state detecting apparatus 100 of this embodiment (FIG. 24). Note that in this specification, the "load detectors placed in the bed" mean the load detectors each of which is provided between one of the four feet of the bed BD and the board of the bed BD as described above and the load detectors each of which is provided between the upper foot portion and the lower foot portion.

Note that in the embodiment described above, it is also allowable to provide a signal amplifying unit for amplifying the load signal fed from the load detecting unit 1 and/or a filtering unit for removing the noise from the load signal, between the load detecting unit 1 and the A/D converting unit 2.

Note that in the body state detecting apparatus 100 of the embodiment described above, the display unit is not limited to a unit which displays the information on the monitor so that the user can make the visual recognition. For example, the display unit 5 may be a printer which periodically prints and outputs the body state of the subject S. Alternatively, the display unit 5 may be a unit which performs the display by using any simple visual expression, for example, such that a blue lamp is turned ON if the subject is in the supine position, a yellow lamp is turned ON if the subject is in the recumbent position, and/or a red lamp is turned ON if the subject is in the prone position. Further alternatively, the display unit 5 may be a unit which reports the body state of the subject S to the user by means of any sound or voice. Further alternatively, it is also allowable that the body state detecting apparatus 100 does not have the display unit 5. The body state detecting apparatus 100 may have only an output terminal for outputting the information such as an image information signal or the like. A monitor (display device) or the like, which is provided to perform the display, will be connected to the body state detecting apparatus 100 by the aid of the output terminal.

Note that the notifying unit 6 of the embodiment described above performs the notification auditorily. However, the notifying unit 6 may be constructed to perform the notification visually by means of, for example, the flashing or flickering of light. Alternatively, the notifying unit 6 may be constructed to perform the notification by means of the vibration. Further, it is also allowable that the body state detecting apparatus 100 of the embodiment described above does not have the notifying unit 6.

Note that the components of the body state detecting apparatus 100 of the embodiment described above, which are connected to one another by means of the wirings, may be connected to one another in a wireless manner.

The body state detecting apparatus 100 of the embodiment and the modified embodiment described above determines the extending direction of the body axis of the subject S and/or the head placement of the subject S on the basis of the load change detected by the load detectors 11 to 14. Hence, according to the body state detecting apparatus 100, 200, it is possible to detect the body state of the subject S in a detailed manner.

According to the body state detecting apparatus 100 of the embodiment and the modified embodiment described above, the head placement determining unit 33 can determine the head placement of the subject S in a more detailed manner on the basis of the direction of the body axis of the subject S determined by the body axis direction determining unit 32. Further, because the sleeping form determining unit 34 is provided, it is possible to detect the body state of the subject S in a more detailed manner.

The body state detecting method of the embodiment and the modified embodiment described above determines the extending direction of the body axis of the subject S and/or the head placement of the subject S on the basis of the load change detected by the load detectors 11 to 14. Hence, according to the body state detecting method of the present disclosure, it is possible to detect the body state of the subject S in a detailed manner.

According to the body state detecting method of the embodiment and the modified embodiment described above, because the head placement of the subject S is determined after the extending direction of the body axis of the subject S is determined, it is possible to determine the head placement of the subject S in a more detailed manner. Further, because of further including the determination of the sleeping form of the subject on the basis of the detected load change, it is possible to detect the body state of the subject S in a more detailed manner.

The body state detecting apparatus using the bed sensors of the embodiment described above can synchronously and simultaneously measure the state of living body information and its temporal change about the body weight, body motion, respiration, snore, heartbeat, and the like, based on the time series data of the load sensors. Therefore, it is also possible to determine the physical condition of the subject under temporal change, at each time, in synchronization with the living body information.

In the body state detecting apparatus described above, the small body motion information determining unit determines the small body motion based on the temporal variation of the center of gravity position from which the large body motion determined by the large body motion information determining unit has been removed. However, in addition thereto or in place thereof, it is also allowable to determine the small body motion on the basis of the direction of movement of the center of gravity position and/or the periodicity based on the influence of the respiration.

The body state detecting apparatus described above can synchronously acquire not only the large body motion information, the small body motion information, and the respiratory rate, but also the body weight, the heartbeat, and the determination result of the physical condition determining unit.

The physical condition determining unit of the body state detecting apparatus described above may determine not only whether the subject is in the sleep state or the wakeful state but also whether or not the subject is in the delirium state, on the basis of the acquired body motion information and/or the respiratory rate of the subject.

A bed leaving/settling determining unit may be provided in the physical condition determining unit of the body state detecting apparatus described above to determine whether or not the subject is present on the bed on the basis of the detected load. The bed leaving/settling determining unit may determine not only the bed leaving/settling but also the body weight and/or the body weight variation of the subject.

The display unit of the body state detecting apparatus of the present disclosure may display the present states and the temporal changes of the acquired body motion information, the body axis direction, the respiration, and the heartbeat of the subject as the history of movement of the center of gravity position on the bed.

The present invention is not limited to the embodiments described above provided that the feature of the present invention is maintained. Other embodiments, which are conceivable within the scope of the technical concept of the present invention, are also included in the scope of the present invention.

The body state detecting apparatus according to the above embodiments may further include a center of gravity position calculating unit which acquires a temporal variation of a center of gravity position of the subject based on the detected load variation, wherein body state detecting unit may determine the extending direction of the body axis of the subject and/or the head placement of the subject based on the temporal variation of the center of gravity position of the subject.

In the body state detecting apparatus according to the above embodiments, the body state detecting unit may include a body axis direction determining unit which determines the extending direction of the body axis of the subject based on either the detected load variation or the temporal variation of the center of gravity position of the subject, and a head placement determining unit which determines the head placement of the subject, in the determined extending direction of the body axis of the subject, based on either the detected load variation or the temporal variation of the center of gravity position of the subject.

In the body state detecting apparatus according to the above embodiments, the body state detecting unit or the head placement determining unit may determine the head placement of the subject based on a waveform exhibiting either the detected load variation or the temporal variation of the center of gravity position of the subject.

In the body state detecting apparatus according to the above embodiments, the waveform may include an inhalation period exhibiting a rising or a falling depending on an inhalation of the subject, an expiration period exhibiting a rising or a falling depending on an expiration of the subject, and a hold period between the inhalation period and the expiration period; and the body state detecting unit or the head placement determining unit may determine the head placement of the subject based on at least one of the inhalation period, the expiration period and the hold period.

The body state detecting apparatus according to the above embodiment may further include a sleeping form determining unit which determines a sleeping form of the subject based on a waveform exhibiting either the detected load variation or the temporal variation of the center of gravity position of the subject.

The body state detecting method according to the above embodiments may further include acquiring a temporal variation of a center of gravity position of the subject based on the detected load variation, wherein determining the extending direction of the body axis of the subject and/or the head placement of the subject based the detected load variation may be determining the extending direction of the body axis of the subject and/or the head placement of the subject based on the temporal variation of the center of gravity position of the subject.

In the body state detecting method according to the above embodiments, the extending direction of the body axis of the subject may be determined based on either the detected load variation or the temporal variation of the center of gravity position of the subject, and then the head placement of the subject may be determined, in the determined extending direction of the body axis of the subject, based on either the detected load variation or the temporal variation of the center of gravity position of the subject.

In the body state detecting method according to the above embodiments, the head placement of the subject may be determined based on a waveform exhibiting either the detected load variation or the temporal variation of the center of gravity position of the subject.

In the body state detecting method according to the above embodiments, the waveform may include an inhalation period exhibiting a rising or a falling depending on an inhalation of the subject, an expiration period exhibiting a rising or a falling depending on an expiration of the subject, and a hold period between the inhalation period and the expiration period; and the head placement of the subject may be determined based on at least one of the inhalation period, the expiration period and the hold period.

In the body state detecting method according to the above embodiments may further include determining a sleeping form of the subject based on a waveform exhibiting either the detected load variation or the temporal variation of the center of gravity position of the subject.

According to the body state detecting apparatus, the body state detecting method and the bed system of one aspect of the present disclosure, it is possible to detect a body state of a subject on a bed in a detailed manner based on a detection performed by the load detectors.

According to the body state detecting apparatus of one aspect of the present disclosure, based only on the detection of the load detectors, it is possible to detect the body state of the subject in a detailed manner. Therefore, it is possible to grasp the state of subject at low cost and without being burdensome for the subject, and thus to facilitate improvement in the quality of medical practice and nursing care. Further, according to the body state detecting apparatus of one aspect of the present disclosure, it is possible to synchronously detect the body motion information and the respiration information such as the respiratory rate or the like, and consequently the inspection items including, for example, the body weight, the heart rate, the snore, and occurrence of the leaving from the bed and the settling on the bed, by using only the load detectors placed under the bed or in the bed. Therefore, it is unnecessary to attach different sensors to the subject for the respective items, and it is unnecessary to synchronize the outputs from a plurality of sensors. Further, it is possible to automatically input the respiratory condition into the nursing record (vital record) and display the same, and it is possible to automatically transmit information on the deterioration of the respiratory condition to the nurse. Therefore, it is possible to decrease the number of times of the checking for the patient at night by the nurse, it is possible to decrease the amount of work of the nurse, and it is possible to improve the quality of the sleep of the patient. Further, for example, when the falling from the bed, the respiratory arrest, the cardiac arrest, or the death, which is not anticipated by the medical staff, occurs, the body state detecting apparatus of one aspect of the present disclosure can also be utilized to investigate the cause thereof.

Further, the present invention can be described in accordance with the following items:

1. A body state detecting apparatus for detecting a body state of a subject on a bed, the apparatus comprising:
a plurality of load detectors which are placed in the bed or under feet of the bed and which detect a load variation depending on a respiration of the subject; and
a body state detecting unit which determines an extending direction of a body axis of the subject and/or a head placement of the subject based on the detected load variation.

2. The body state detecting apparatus according to item 1, further comprising a center of gravity position calculating unit which acquires a temporal variation of a center of gravity position of the subject based on the detected load variation, wherein the body state detecting unit determines the extending direction of the body axis of the subject and/or the head placement of the subject based on the temporal variation of the center of gravity position of the subject.

3. The body state detecting apparatus according to item 1 or 2, wherein the body state detecting unit includes a body axis direction determining unit which determines the extending direction of the body axis of the subject based on either the detected load variation or the temporal variation of the center of gravity position of the subject, and a head placement determining unit which determines the head placement of the subject, in the determined extending direction of the body axis of the subject, based on either the detected load variation or the temporal variation of the center of gravity position of the subject.

4. The body state detecting apparatus according to any one of items 1 to 3, wherein the body state detecting unit or the head placement determining unit determines the head placement of the subject based on a waveform exhibiting either the detected load variation or the temporal variation of the center of gravity position of the subject.

5. The body state detecting apparatus according to item 4, wherein the waveform includes an inhalation period exhibiting a rising or a falling depending on an inhalation of the subject, an expiration period exhibiting a rising or a falling depending on an expiration of the subject, and a hold period between the inhalation period and the expiration period; and the body state detecting unit or the head placement determining unit determines the head placement of the subject based on at least one of the inhalation period, the expiration period and the hold period.

6. The body state detecting apparatus according to any one of items 1 to 5, further comprising a sleeping form determining unit which determines a sleeping form of the subject based on a waveform exhibiting either the detected load variation or the temporal variation of the center of gravity position of the subject.

7. A bed system comprising:
a bed; and
the body state detecting apparatus according to any one of items 1 to 6.

8. A body state detecting method for detecting a body state of a subject on a bed, the method comprising:
detecting a load variation depending on a respiration of the subject with a plurality of load detectors placed in the bed or under feet of the bed; and
determining an extending direction of a body axis of the subject and/or a head placement of the subject based on the detected load variation.

9. The body state detecting method according to item 8, further comprising acquiring a temporal variation of a center of gravity position of the subject based on the detected load variation, wherein determining the extending direction of the body axis of the subject and/or the head placement of the subject based on the detected load variation is determining the extending direction of the body axis of the subject and/or the head placement of the subject based on the temporal variation of the center of gravity position of the subject.

10. The body state detecting method according to item 8 or 9, wherein the extending direction of the body axis of the subject is determined based on either the detected load variation or the temporal variation of the center of gravity position of the subject, and then the head placement of the subject is determined, in the determined extending direction of the body axis of the subject, based on either the detected load variation or the temporal variation of the center of gravity position of the subject.

11. The body state detecting method according to any one of items 8 to 10, wherein the head placement of the subject is determined based on a waveform exhibiting either the detected load variation or the temporal variation of the center of gravity position of the subject.

12. The body state detecting method according to item 11, wherein the waveform includes an inhalation period exhibiting a rising or a falling depending on an inhalation of the subject, an expiration period exhibiting a rising or a falling depending on an expiration of the subject, and a hold period between the inhalation period and the expiration period; and the head placement of the subject is determined based on at least one of the inhalation period, the expiration period and the hold period.

13. The body state detecting method according to any one of items 8 to 12, further comprising determining a sleeping form of the subject based on a waveform exhibiting either the detected load variation or the temporal variation of the center of gravity position of the subject.

14. A body state detecting apparatus for detecting a body state of a subject on a bed, the apparatus comprising:
a plurality of load detectors which are placed in the bed or under feet of the bed and which detect a load variation depending on a respiration of the subject; and
a body state detecting unit which determines an extending direction of a body axis of the subject based on the detected load variation.

The invention claimed is:
1. A body state detecting apparatus for detecting a body state of a subject on a bed, the apparatus comprising:
a plurality of load detectors which are placed in the bed or under feet of the bed and which detect a load variation depending on a respiration of the subject; and
a controller including
a body state detecting unit which determines an extending direction of a body axis of the subject and a head placement of the subject based on the detected load variation; and
a center of gravity position calculating unit which acquires a temporal variation of a center of gravity position of the subject based on the detected load variation, wherein the body state detecting unit includes a body axis direction determining unit which determines the extending direction of the body axis of the subject based on a direction in which the center of gravity position of the subject oscillates, and a head placement determining unit which determines the head placement of the subject, in the determined extending direction of the body axis of the subject, based on the detected load variation.

2. The body state detecting apparatus according to claim 1, wherein the head placement determining unit determines the head placement of the subject based on a waveform exhibiting the detected load variation.

3. The body state detecting apparatus according to claim 1,
wherein the body axis direction determining unit determines the extending direction of the body axis of the subject based on a temporal variation of the center of gravity position of the subject and/or the head placement determining unit determines the head placement of the subject based on the temporal variation of the center of gravity position of the subject.

4. The body state detecting apparatus according to claim 3, wherein the head placement determining unit determines the head placement of the subject based on a waveform exhibiting the temporal variation of the center of gravity position of the subject.

5. A body state detecting apparatus for detecting a body state of a subject on a bed, the apparatus comprising:
a plurality of load detectors which are placed in the bed or under feet of the bed and which detect a load variation depending on a respiration of the subject; and
a controller including a body state detecting unit which determines an extending direction of a body axis of the subject and a head placement of the subject based on the detected load variation,
wherein the body state detecting unit determines the head placement of the subject based on a shape of a wave corresponding to one respiration cycle included in a waveform exhibiting the detected load variation.

6. The body state detecting apparatus according to claim 5, further comprising a center of gravity position calculating unit which acquires a temporal variation of a center of gravity position of the subject based on the detected load variation,
wherein the body state detecting unit determines the extending direction of the body axis of the subject based on the temporal variation of the center of gravity position of the subject, and/or determines the head placement of the subject based on a waveform exhibiting the temporal variation of the center of gravity position of the subject.

7. The body state detecting apparatus according to claim 2, wherein the waveform exhibiting the detected load variation includes an inhalation period exhibiting a rising or a falling depending on an inhalation of the subject, an expiration period exhibiting a rising or a falling depending on an expiration of the subject, and a hold period between the inhalation period and the expiration period; and
the head placement of the subject is determined based on at least one of the inhalation period, the expiration period and the hold period.

8. The body state detecting apparatus according to claim 1, further comprising a sleeping form determining unit which determines a sleeping form of the subject based on a waveform exhibiting the detected load variation.

9. The body state detecting apparatus according to claim 4, wherein the waveform exhibiting the temporal variation of the center of gravity position includes an inhalation period exhibiting a rising or a falling depending on an inhalation of the subject, an expiration period exhibiting a rising or a falling depending on an expiration of the subject, and a hold period between the inhalation period and the expiration period; and
the head placement of the subject is determined based on at least one of the inhalation period, the expiration period and the hold period.

10. The body state detecting apparatus according to claim 3, further comprising a sleeping form determining unit which determines a sleeping form of the subject based on the waveform exhibiting the temporal variation of the center of gravity position of the subject.

11. A bed system comprising:
a bed; and
the body state detecting apparatus according to claim 1.

12. A body state detecting method for detecting a body state of a subject on a bed, the method comprising:
detecting a load variation depending on a respiration of the subject with a plurality of load detectors placed in the bed or under feet of the bed;
determining an extending direction of a body axis of the subject and a head placement of the subject based on the detected load variation; and
acquiring a temporal variation of a center of gravity position of the subject based on the detected load variation
wherein the extending direction of the body axis of the subject is determined based on a direction in which the center of gravity position of the subject oscillates, and then the head placement of the subject is determined, in the determined extending direction of the body axis of the subject, based on the detected load variation.

13. The body state detecting method according to claim 12, wherein the head placement of the subject is determined based on a waveform exhibiting the detected load variation.

14. The body state detecting method according to claim 12,
wherein the determining of the extending direction of the body axis of the subject and/or the head placement of the subject based on the detected load variation includes determining the extending direction of the body axis of the subject and/or the head placement of the subject based on the temporal variation of the center of gravity position of the subject.

15. The body state detecting method according to claim 14, wherein the head placement of the subject is determined based on a waveform exhibiting the temporal variation of the center of gravity position of the subject.

16. A body state detecting method for detecting a body state of a subject on a bed, the method comprising:
detecting a load variation depending on a respiration of the subject with a plurality of load detectors placed in the bed or under feet of the bed; and
determining an extending direction of a body axis of the subject and a head placement of the subject based on the detected load variation,
wherein the head placement of the subject is determined based on a shape of a wave corresponding to one respiration cycle included in a waveform exhibiting the detected load variation.

17. The body state detecting method according to claim 16, further comprising acquiring a temporal variation of a center of gravity position of the subject based on the detected load variation,
wherein the determining of the extending direction of the body axis of the subject and/or the head placement of the subject based on the detected load variation includes determining the extending direction of the body axis of the subject based on the temporal variation of the center of gravity position of the subject and/or determining the head placement of the subject based on a waveform exhibiting the temporal variation of the center of gravity position of the subject.

18. The body state detecting method according to claim 13, wherein the waveform exhibiting the detected load variation includes an inhalation period exhibiting a rising or a falling depending on an inhalation of the subject, an expiration period exhibiting a rising or a falling depending on an expiration of the subject, and a hold period between the inhalation period and the expiration period; and the head placement of the subject is determined based on at least one of the inhalation period, the expiration period and the hold period.

19. The body state detecting method according to claim 12, further comprising determining a sleeping form of the subject based on a waveform exhibiting the detected load variation.

20. The body state detecting method according to claim 15, wherein the waveform exhibiting the temporal variation of the center of gravity position includes an inhalation period exhibiting a rising or a falling depending on an inhalation of the subject, an expiration period exhibiting a rising or a falling depending on an expiration of the subject, and a hold period between the inhalation period and the expiration period; and the head placement of the subject is determined based on at least one of the inhalation period, the expiration period and the hold period.

21. The body state detecting method according to claim 14, further comprising determining a sleeping form of the subject based on a waveform exhibiting the temporal variation of the center of gravity position of the subject.

22. A body state detecting apparatus for detecting a body state of a subject on a bed, the apparatus comprising:
 a plurality of load detectors which are placed in the bed or under feet of the bed and which detect a load variation depending on a respiration of the subject; and
 a controller including a body state detecting unit which determines a head placement of the subject based on the detected load variation,
 wherein the body state detecting unit determines the head placement of the subject based on a shape of a wave corresponding to one respiration cycle included in a waveform exhibiting the detected load variation.

* * * * *

UNITED STATES PATENT AND TRADEMARK OFFICE
CERTIFICATE OF CORRECTION

PATENT NO.        : 10,390,735 B2
APPLICATION NO.   : 15/880947
DATED             : August 27, 2019
INVENTOR(S)       : Hiroyuki Akatsu et al.

Page 1 of 1

It is certified that error appears in the above-identified patent and that said Letters Patent is hereby corrected as shown below:

On the Title Page

Item (73) Assignee: "MINEBEA MITSUMI INC., Nagano, Japan (JP)" should read -- MINEBEA MITSUMI INC., Nagano (JP); NATIONAL UNIVERSITY CORPORATION CHIBA UNIVERSITY, CHIBA (JP) --

Signed and Sealed this
Fourth Day of August, 2020

Andrei Iancu
*Director of the United States Patent and Trademark Office*